(12) United States Patent
Novotny

(10) Patent No.: US 9,995,718 B1
(45) Date of Patent: Jun. 12, 2018

(54) CHEMICAL AND BIOMEDICAL NANOSENSORS

(71) Applicant: Vlad Joseph Novotny, Los Gatos, CA (US)

(72) Inventor: Vlad Joseph Novotny, Los Gatos, CA (US)

(73) Assignee: Vlad Novotny, Los Gatos, CA (US)

( * ) Notice: Subject to any disclaimer, the term of this patent is extended or adjusted under 35 U.S.C. 154(b) by 0 days. days.

(21) Appl. No.: 14/824,311

(22) Filed: Aug. 12, 2015

Related U.S. Application Data

(62) Division of application No. 13/209,442, filed on Aug. 15, 2011, now Pat. No. 9,140,667.

(60) Provisional application No. 61/373,851, filed on Aug. 15, 2010.

(51) Int. Cl.
| | |
|---|---|
| *G01N 29/036* | (2006.01) |
| *G01N 29/24* | (2006.01) |
| *G01N 29/02* | (2006.01) |

(52) U.S. Cl.
CPC ....... *G01N 29/2437* (2013.01); *G01N 29/022* (2013.01); *G01N 2291/014* (2013.01); *G01N 2291/0255* (2013.01); *G01N 2291/0256* (2013.01); *G01N 2291/0257* (2013.01); *G01N 2291/02416* (2013.01); *G01N 2291/02466* (2013.01)

(58) Field of Classification Search
CPC ....... G01N 29/022; G01N 2291/02466; G01N 2291/02416; G01N 2291/0255; G01N 2291/0256; G01N 2291/0257; B28Y 15/00
USPC ........... 73/24.06, 61.45, 61.49, 61.71, 61.75, 73/61.79, 64.53
See application file for complete search history.

(56) References Cited

U.S. PATENT DOCUMENTS

| | | | | |
|---|---|---|---|---|
| 2003/0119220 | A1* | 6/2003 | Mlcak ................ | B81B 3/0089 438/52 |
| 2005/0160821 | A1* | 7/2005 | Cunningham ....... | G01N 29/022 73/652 |
| 2005/0161749 | A1* | 7/2005 | Yang .................... | B81B 3/0035 257/414 |
| 2005/0196877 | A1* | 9/2005 | Weinberg ......... | G01N 33/54373 436/518 |
| 2006/0260386 | A1* | 11/2006 | Cunningham ....... | G01N 29/022 73/24.06 |

* cited by examiner

*Primary Examiner* — Manish S Shah
*Assistant Examiner* — Rose M Miller

(57) ABSTRACT

The electrostatic sensors of bridge or cantilever type with multiple electrodes, the electrostatic sensors of comb type and piezoelectric sensors are used for the single molecule detection of ligands. The electrical driving of sensors is separated in some cases from the sensing for increased sensitivity. The large arrays of sensors with individual or common sensing circuits are employed to further improve detection sensitivity. The fabrication of the sensors, their functionalization for detection of many chemical and biological species and electrical circuitry, packaging, microfluidic subsystem and the system architecture are also disclosed. The individual, specific sensing of single species or simultaneous detection of multiple species is realized. The freeze drying or critical point drying after exposure of sensors to ligands present in liquids and detection in reduced pressure or vacuum is employed for increased sensitivity, down to the single molecule.

21 Claims, 24 Drawing Sheets

Initial State
120

Physical Adsorption or Chemical Reaction
130

Final State Detection
140

Side View

Top View

Side View

Top View

Side View

Top View

Side View

Top View

Side View

Top View

Side View

Top View

Side View

Top View

Side View

Top View

Side View

Top View

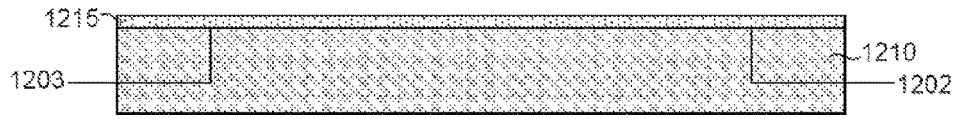
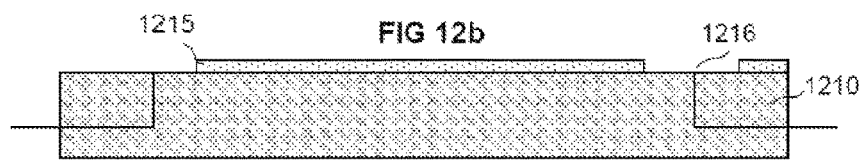
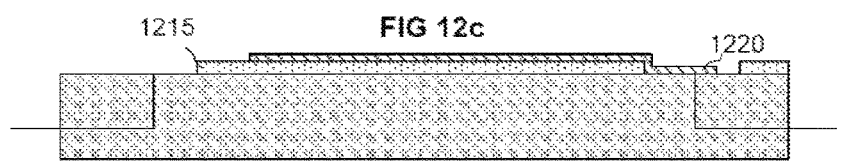
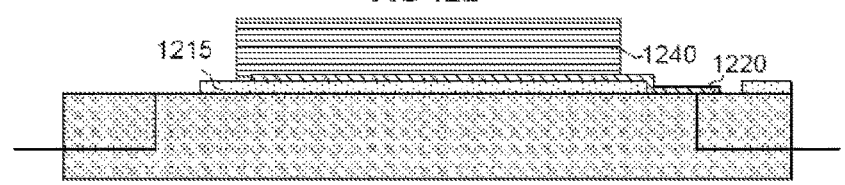
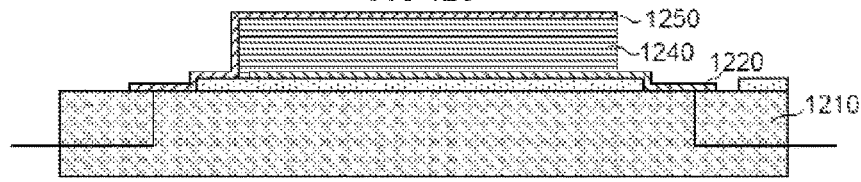
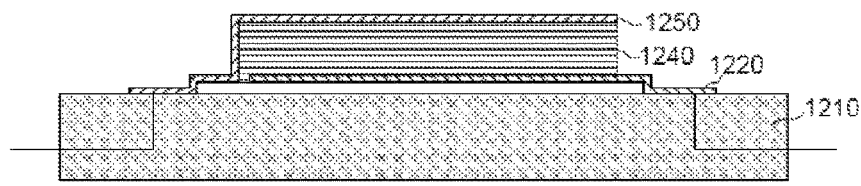

Initial State

Physical Adsorption or Chemical Reaction

Final State Detection

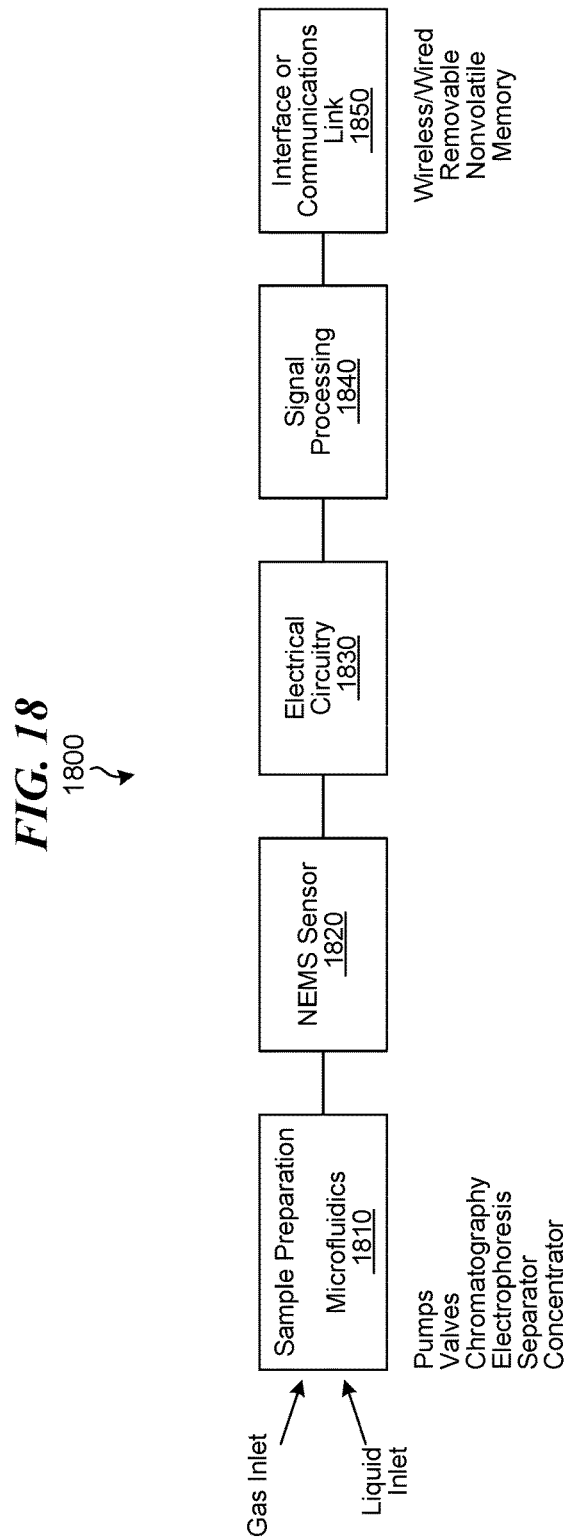

CHEMICAL AND BIOMEDICAL NANOSENSORS

RELATED U.S. APPLICATION DATA

Utility application Ser. No. 13/209,442 filed on Aug. 15, 2011.

Provisional application No. 61/373,851 filed on Aug. 15, 2010.

BACKGROUND

This description relates to Nano-Electro-Mechanical Systems (NEMS) and Complementary Metal Oxide Semiconductor (CMOS) circuitry for detection of chemical and biological agents, referred to as ligands, with sensitivity down to one molecule. NEMS are sensors or actuators that have critical dimensions in nanometer range.

Sensitive detection of gases such as explosive vapors and environmental pollution in ambient environment normally requires sophisticated and expensive instrumentation. Such detection is usually carried out with optical spectrometers or quadrupole, ion trap or time of flight mass spectrometers.

Detection of biological agents is typically performed in liquids using chemical or biological assays that rely on the detection of intrinsic or covalently-attached fluorescent or ultraviolet labels, chemical or electrochemical luminescence, or radioactive labels. These approaches often limit the sensitivity of the assay method and also require expensive equipment. Detection of biological agents can be also performed without labeling with techniques such as surface plasmon resonance, waveguide resonance, electrochemical methods, but such techniques have typically lower sensitivity than labeled methods and similar limitations.

None of these conventional techniques is sufficiently sensitive to detect single molecules or have sufficient resolution to differentiate between molecules that differ in mass by several atomic mass units. The equipment used is not portable or easily operated by the non-specialist. Therefore, these techniques are unsuitable for many personalized wellness, personalized medical and other mobile applications. Portable, robust, easy-to-use clinical measurements enable individuals and medical facilities such as doctor's offices, pharmacies, and diagnostic laboratories to obtain clinically meaningful information reliably and at low cost. There is need to realize detection with the simple devices that have extreme sensitivity for chemical or biological molecules (such as proteins), and small biological agents (e.g., viruses and bacteria), with very inexpensive device.

SUMMARY

The electrostatic resonators of bridge, cantilever and comb types and piezoelectric resonators are used as key components of sensors to detect chemical and biological analytes that range from very small molecules to organic particulates (e.g. virus particles, bacteria, and mammalian cells). The detection is based on sensing frequency change associated with mass increase due to specific interaction of these materials with receptors that are attached to resonators. Large arrays of sample and reference sensors, fast, low power detection sensing circuits and optional low pressure or vacuum environment providing high resonant quality factors during measurements are employed for very sensitive detection. The fabrication of the sensors, their functionalization for detection of many chemical and biological species and electrical circuitry, packaging, and microfluidic system architecture are also described. The static or kinetic detection of ligands is also possible with these sensors.

DESCRIPTION OF DRAWINGS

FIG. 12a to FIG. 12f represent outline of the fabrication process for piezoelectric nanosensors using separate fabrication of NEMS and CMOS wafers.

FIG. 18 is the system diagram of the architecture for detection of single molecules, viruses or bacteria.

DETAILED DESCRIPTION

Figure 1A:
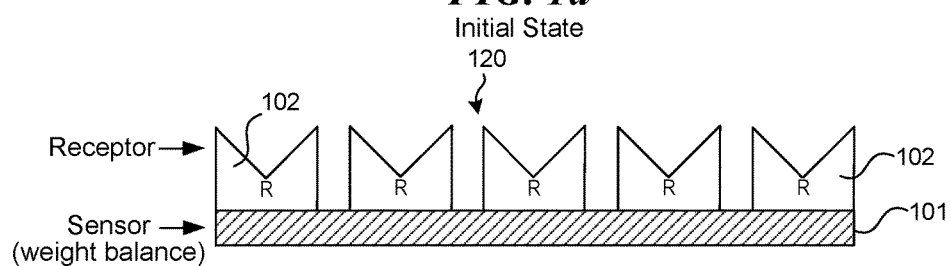
FIG. 1a to FIG. 1c show schematic operational principles for detection of ligands, L, by change of mass of a sensor resulting from physical adsorption or chemical reaction of ligands with receptors, R, present on the sensor.
Figure 1B:
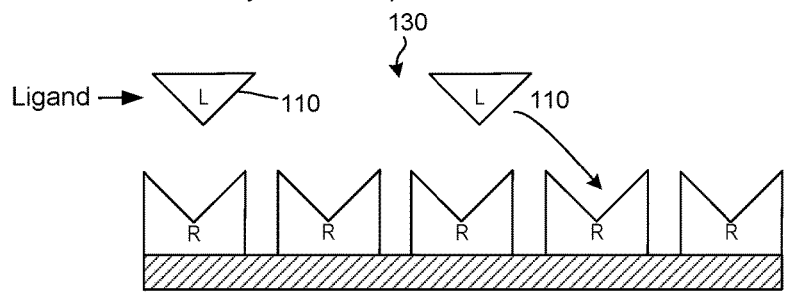
Figure 1C:
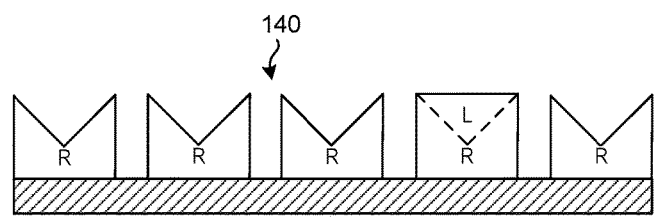

The operational principle for the detection of chemical and biological species also referred to here as ligands, L, is shown in FIG. 1. Chemical agents on the surface of the sensor 101 are referred to as receptors, R. This figure shows a receptor, R, 102 interacting with a ligand, L, 110, at the sensor surface 101. This interaction is the result of either specific noncovalent binding or by chemical reaction between receptor and ligand on the surface of the sensor 101. Specific binding between receptor and ligand is illustrated schematically in FIG. 1c.

The receptors, R, 102 are selected so that they will interact only with specific ligands, L, 110. Receptors are deposited on one surface of the sensor as shown in FIG. 1, or on all surfaces of the sensor or are deposited only in known, specific locations on the sensor surface. The initial state of the sensor 120 with deposited receptors 102, state 130 after introduction of ligands 110 and the final, bound state 140 are depicted in FIG. 1a, b and c respectively. In another case, the receptors 102 can be deposited only in the specific location for simplified detection, but with much lower sensitivity. Ideally, the ligands, L, are distinguishable because noncovalent binding or chemical reactions are specific for particular ligands and the sensing system has sufficient sensitivity to differentiate closely related compounds that have similar mass. In yet another case, receptor, R, mixed with ligand, L, in solution, inhibits the interaction of ligand, L with the sensor-bound receptor, R.

Upon binding, the mass of the ligand is added to the total weight of the sensor. This change alters sensor response, such as its resonance frequency. This principle can be applied in the detection of a wide variety of chemical and biological analytes. For example, this type of sensor detects either antibodies or their respective antigens, enzymes or their respective substrates/inhibitors, hormone ligands or their respective receptors, cells or cellular effectors, viral particles or biomolecules and biological molecules that specifically bind to viral proteins at the particle surface. In all cases, one of the binding components is fixed to the sensor surface; the other component is added in solution, suspension, or emulsion.

The detection of chemical and biological species is based on the determination of change of resonant frequency of the bridge, cantilever, electrostatic comb or piezoelectric sensor caused by adsorption or reaction of the ligands, L, with the receptors, R, on the bridge, cantilever, comb or piezoelectric sensor surface.

Figure 2A:
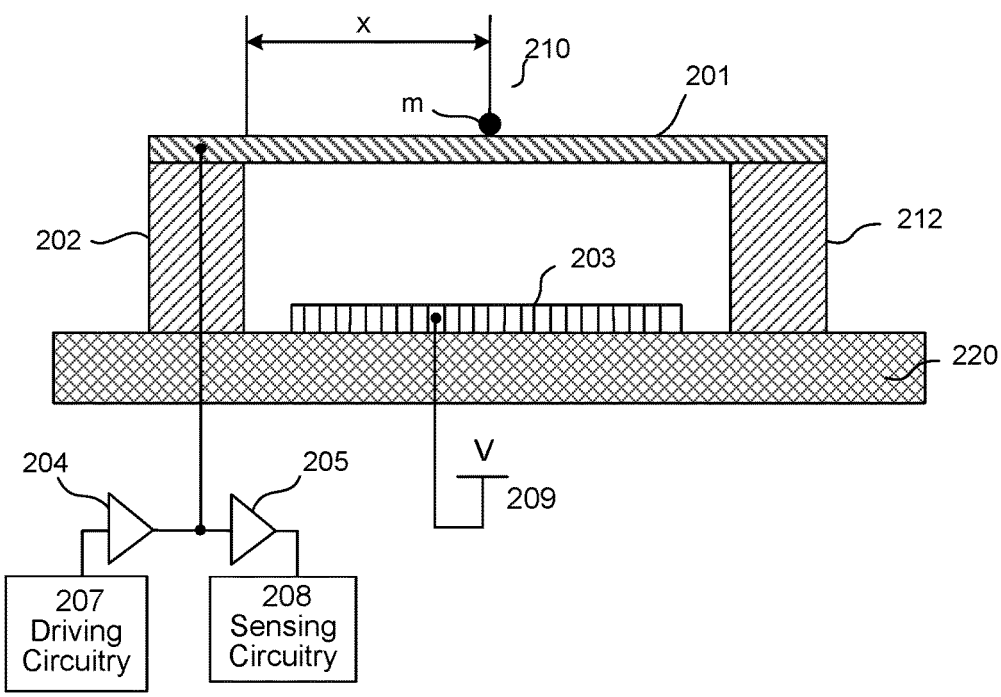
FIG. 2a is a side view and FIG. 2b is a top view schematic of a single element of a bridge nanosensor array and detection circuitry for sensing of adsorbed or reacted species.
Figure 2B:
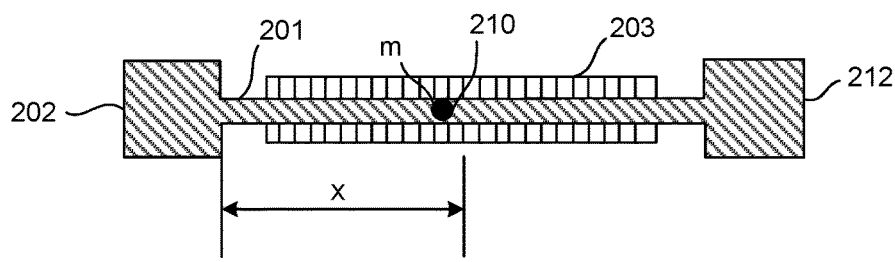

The first implementation of the electrostatic detection of mass increase with the bridge type of sensor is shown schematically in FIG. 2 with basic geometry according to the prior art. The electrically conductive bridge 201, forming one electrode of the sensing structure, is supported on the electrically conducting posts 202 and 212 that reside on the substrate 220. The second electrode 203 is positioned under the bridge electrode 201 on the substrate 220 and is connected to the driving circuitry 207. The driving voltage signal from the driving circuit is amplified with amplifier 204 and applied to one of two electrodes. The bridge 201 is connected electrically to the sensing circuit 208 through the electrically conducting posts 202 and 212 and amplifier 205.

The driving circuit 204 and 207 and sensing circuit 205 and 208 can be alternatively connected to the electrode 203. The electrical potential difference between the electrically conductive bridge 201 and the electrode 203 creates electric field between them and the beam 201 can be set into oscillatory motion with oscillatory driving waveform. When the driving waveform has sufficient energy at the resonant frequency of the bridge 201, then the bridge oscillates with large displacements at that resonant frequency. Alternatively, the driving waveform can have energy at a harmonic of the fundamental resonant frequency that allows detection at higher frequency and potentially higher detection sensitivity.

When the ligand 210 is adsorbed on or reacted onto the bridge 201, then resonant frequency f of the beam decreases by $\Delta f$. The change of resonant frequency $\Delta f$ is related to the mass change m of the mass of the bridge M. Depending on resolution of frequency detection $\Delta f$, many chemical and biological molecules can be determined from the measured change in frequency.

The change in the resonant frequency is detected with CMOS circuitry 208 that is placed adjacent to, below or above NEMS device. The several different methods can be used to measure sensitively the frequency shift. The preferred methods are described below.

When the ligands are introduced in the gas phase, molecules present in the ambient or in the specific gaseous environment can be identified. When the unknown biological ligands are brought into contact with bridge in aqueous or other liquid environment, the unknown biological species can be identified in principle. Consequently, the vibrating bridge serves as a basic element of the nano mass spectrometer for identification of chemical and biological species. Similar implementation can be realized with the substitution of the bridge by the cantilever or comb described below. Nano mass spectrometer is defined here as the sensor that measures very small changes in its mass as a result of interaction of the ligands with specific receptors on sensor and allows identification of the ligands.

For the geometric dimensions of the beam with the length D, the width W and thickness T, the mechanical stiffness of the bridge $S_b$ and the cantilever $S_c$ are $$S_c = E \cdot W \cdot T^3 / (4 \cdot D^3)$$

$$S_b = 81 \cdot E \cdot W \cdot T^3 / (6 \cdot D^3)$$

respectively, when T<W.

The resonant frequency f is given by $$f = (1/(2 \cdot \pi)) \sqrt{(S_{b,c}/M)},$$

where E is the Young modulus of the beam and M is the mass of the beam or sensor with receptors before interaction with ligands. When operations at high resonant frequencies are desired, the bridge beam is used rather than cantilever beam, as bridge configuration has the stiffness that is about 54 times higher than cantilever configuration, resulting in the resonant frequency being almost 8 times higher for the same basic geometric dimensions. Optionally, the dimensions of the bridge or cantilever beam can be adjusted to set the resonant frequency to the desired level. The typical dimensions of the individual sensors are: D=1 to 10 um, W=100 to 1000 nm and T=1 to 100 nm, resulting in the fundamental resonant frequency of the bridge resonator from 1 MHz to 30 GHz.

When molecular ligand with mass m is adsorbed onto the bridge at the mid point between two posts 202 and 212, then the resonant frequency of the beam decreases by Δf where $$\Delta f = (1/(2 \cdot \pi))[\sqrt{(S_b \cdot c/M)} - \sqrt{(S_b \cdot c/(M+m))}]$$

The mass m can be then derived from the above equations for f and Δf and the ligand with the mass m can be identified. Statistically, the adsorption or reaction will rarely occur precisely in the middle of the beam when the beam has been functionalized on the whole surface, and additional information is required to relate smaller Δf, than Δf given in the above equation, to the mass m.

Figure 3:
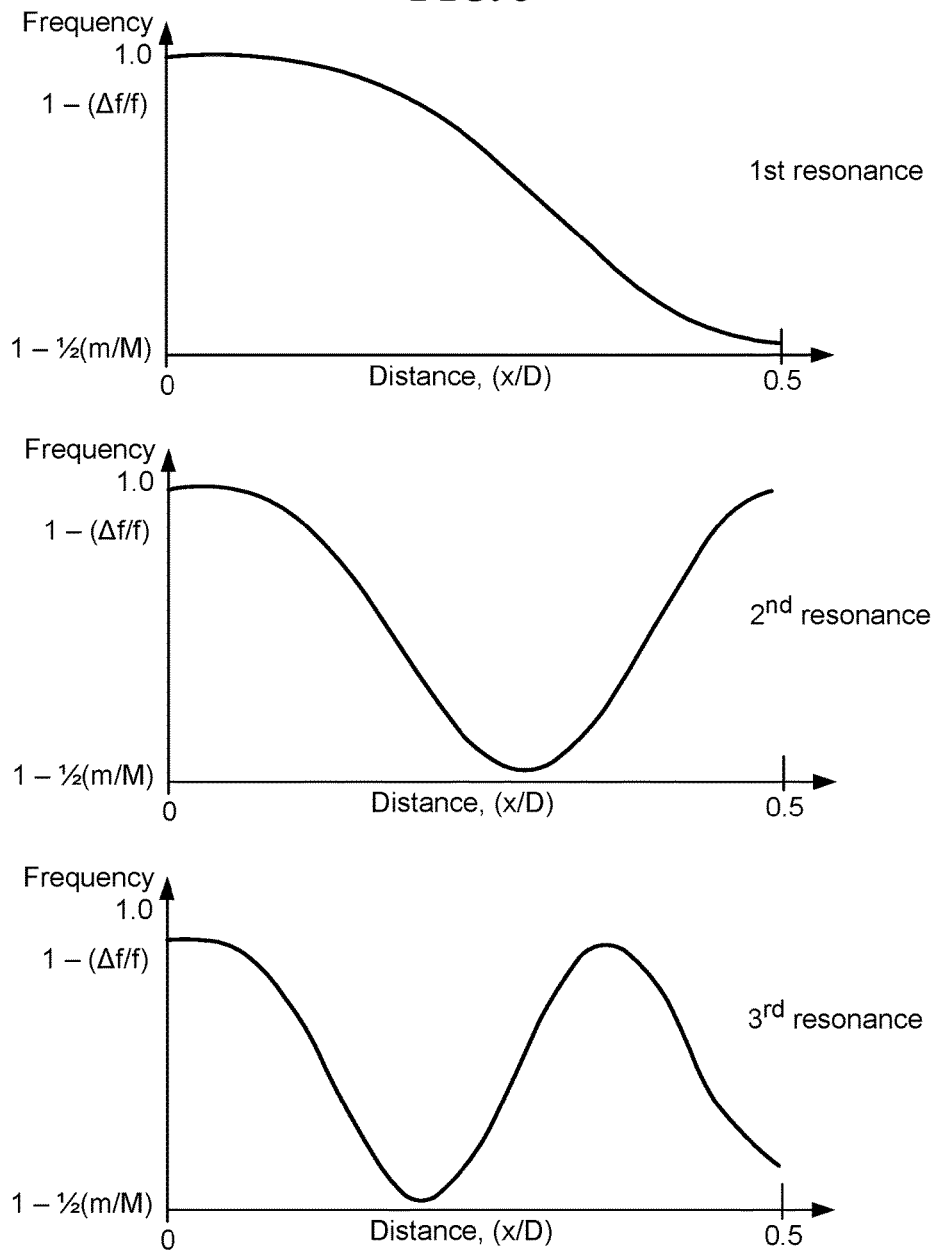
FIG. 3 shows dependence of the resonant frequency of the bridge on the position of the mass m on the bridge.

The dependence of (f−Δf) divided by the resonant frequency, f, on the position of adsorbed or reacted ligand m on the beam at the position x from the post is shown in FIG. 3. (f−Δf)/f=1−(Δf/f) varies from 1.0 when the ligand resides on the post at x/D=0 to about 1−½ (m/M) when the ligand is in the middle of the beam at x/D=0.5. When the beam is allowed to resonate at the second harmonic and third harmonic frequency, then the frequency of the resonating bridge varies with distance as shown in FIG. 3. Several new approaches are described below with the architectures that do not have the dependence on the location of the ligands and with configurations that provide determination of the position of the ligand x in addition to Δf.

When many ligands are adsorbed on the bridge or reacted with the bridge surface, so that the surface of the bridge is covered completely by the saturated monolayer of receptor-ligand pairs on top only or both on top and bottom surfaces, then the position where adsorbed/reacted species landed does not have to be known. If sensitivity of detection is high enough to detect a single molecule, the changes of frequency Δf associated with adsorption/reaction of individual ligands can be identified and followed until the process does not yield any further decreases of measured frequency, i.e. the measured frequency has stabilized and does not decrease any more.

Figure 4A:
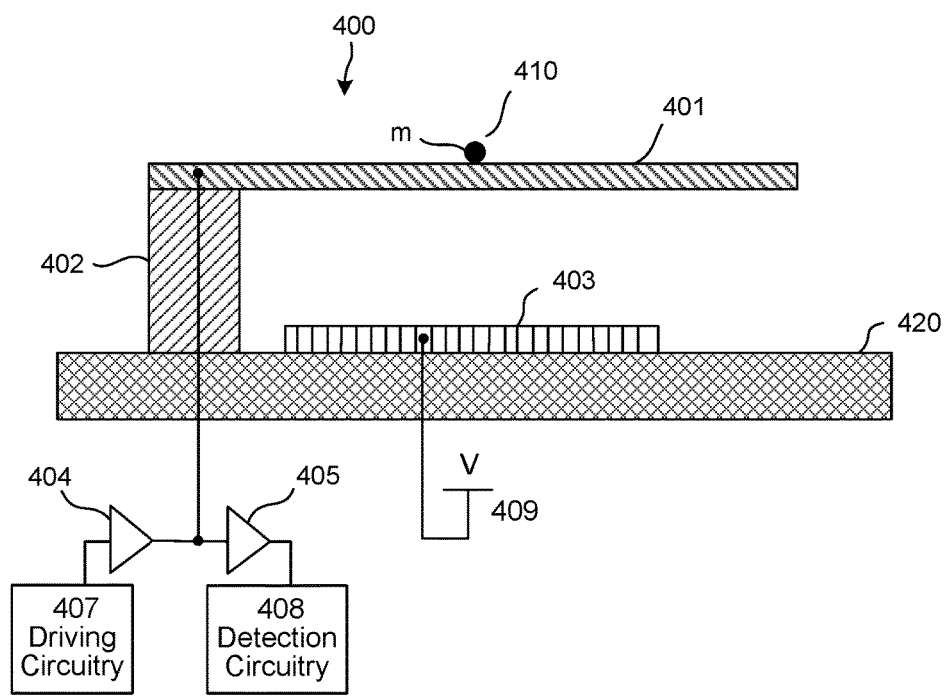
FIG. 4a is a side view and FIG. 4b is a top view schematic of a single element of the cantilever nanosensor array and detection circuitry for sensing of the adsorbed or reacted species.
Figure 4B:
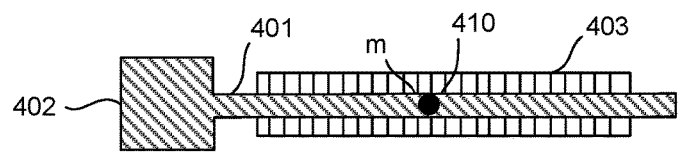

Another implementation of nano mass spectrometer 400 according to the prior art is shown in FIG. 4 where the bridge sensing element 201 is substituted by cantilever sensing element 401. The principle of operation is the same for the cantilever spectrometer, as for the bridge spectrometer. The change of resonant frequency Δf is detected with CMOS detection circuit 408 and 405 while the driving circuit 404 and 407 sets the cantilever into the vibrational motion by the electric field between the electrode 403 and the cantilever beam electrode 401.

The main difference between cantilever and bridge embodiment is the basic operational frequency, with cantilever first resonant frequency being about 7.3 times lower than the bridge resonant frequency for the same dimensions (length, width and thickness) of the bridge and cantilever. Similar resonant frequencies of the cantilever as those of the bridge can be obtained by choosing appropriately shorter length and/or increased thickness and width.

When only a single or a small number of molecules adsorb/react with the bridge or cantilever surface, the location where the adsorption/reaction occurred is best determined experimentally.

Figure 5A:
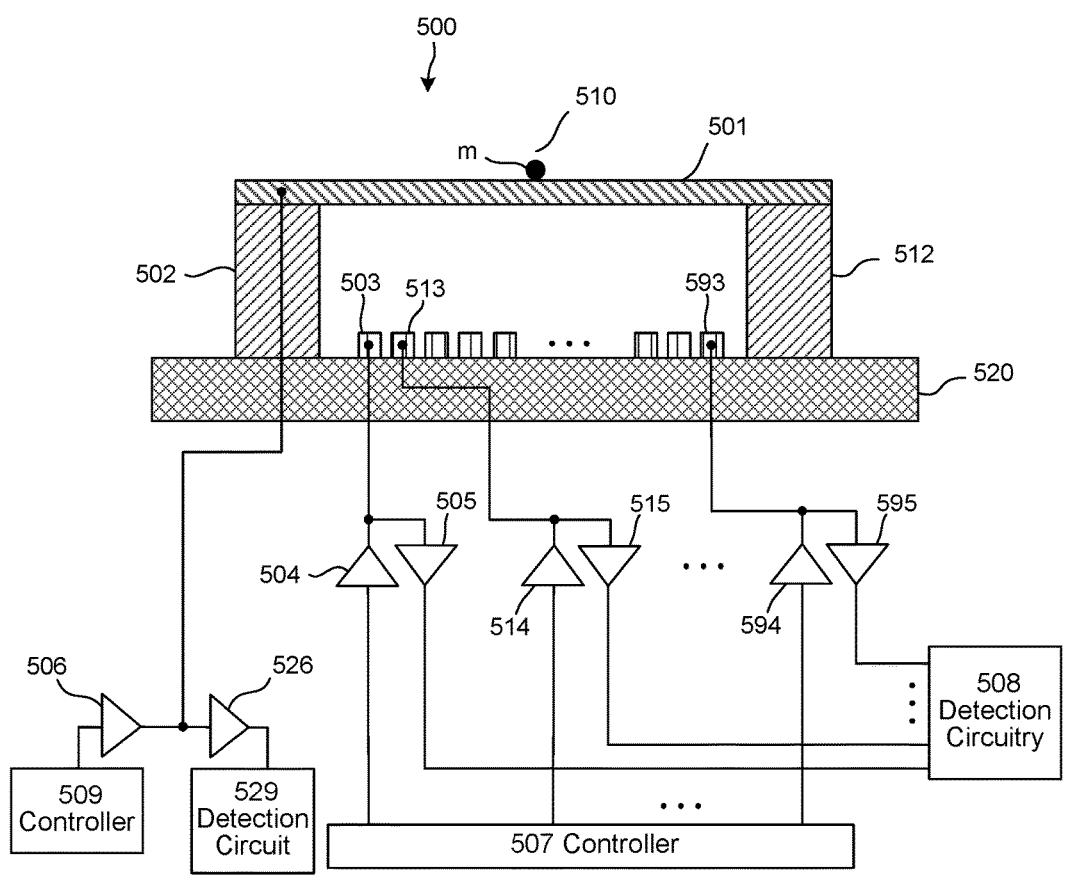
FIG. 5a is a side view and FIG. 5b is a top view schematic of a single element of the bridge nanosensor array with multiple driving electrodes for sensing of mass and position of detected molecule.
Figure 5B:
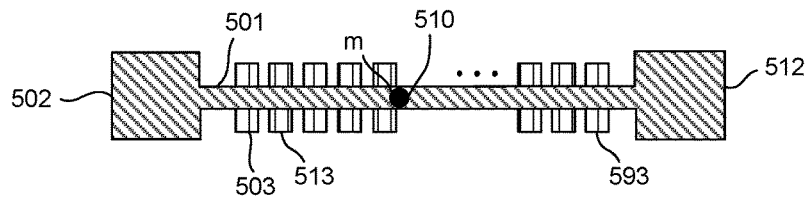

The first approach to determine both mass m and the location x is presented in FIG. 5. The side view of the sensor is shown in FIG. 5a and the top view in FIG. 5b. The sensor 500 has the electrode 203 in FIG. 2 substituted by the array of the electrodes 503, 513, . . . 593. These electrodes can be driven by the CMOS controller 507 and driving amplifiers 504, 514, . . . 594. Alternatively, the electrode 501 can be driven using the controller 509 and amplifier 506. The frequency changes of the bridge resonator 500 are measured using the amplifiers 505, 515, . . . 595 connected to the detection circuit 508. Alternatively, the sensing amplifier 526 connected to the electrode 501 and the detection circuit 529 can be used to supplement measurements of frequency changes. The single electrodes 503 or 513, . . . 593, or pairs of electrodes such as 503+513, 513+523, 503+523, . . . or three electrodes or up to all available electrodes can be driven at the same time with the voltage waveforms applied versus the bridge electrode 501. The signals are taken between the bridge electrode 501 and the single electrodes 503, . . . 593, between 501 and pairs of electrodes 503+513, and between multiple electrodes 503+513+523 . . . . Finite Element Analysis (FEA) is used to predict the changes of the measured frequency based on the different position of mass m 510 on the bridge or cantilever and the least square analysis is performed to match the best fit of FEA prediction with experimental data to determine the increase of mass m and its location x. This analysis is very deterministic because only two unknowns—m and x have to be identified while many (N) matches between FEA and experimental data need to be satisfied.

Figure 6A:
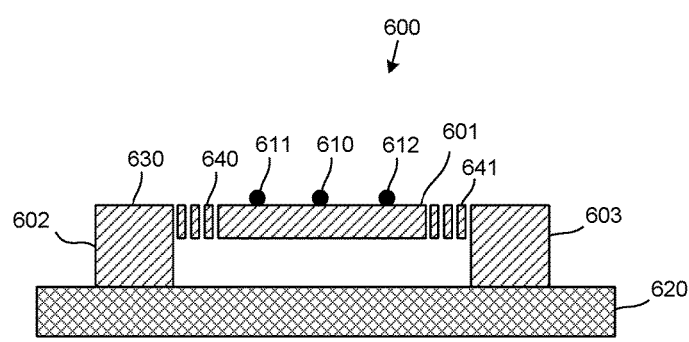
FIG. 6a is a side view and FIG. 6b is a top view schematic of a single element of the electrostatic comb nanosensor array with the single moving electrostatic tooth and detection circuitry.
Figure 6B:
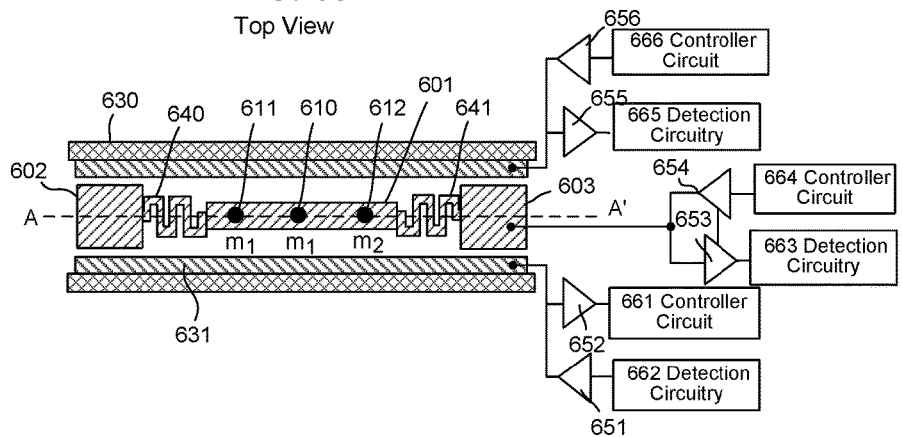

Another approach to determine m without dependence on x, is to use the nano mass spectrometer design that does not have the dependence on the location of adsorbed/reacted ligands. Such a structure is shown in FIG. 6 with electrostatic comb sensor 600. The side view of the sensor 600 is shown in FIG. 6a and the top view is in FIG. 6b. The sensor is composed of the central plate 601 and two sets of hinges 640 and 641 that are attached to each side of the central plate 601 and connected to the posts 602 and 603. The mechanical stiffness of the central plate 601 is orders of magnitude greater than the stiffness of the hinges 640 and 641. The central plate 601 and hinges 640 and 641 are surrounded on both sides with two electrodes 630 and 631, thus forming one tooth electrostatic comb actuator. When the driving voltage is applied with the controller circuit 661 or 664 or 666 and the corresponding amplifiers 651 or 654 or 656 to the electrodes 631 or 601 or 630 respectively, the comb tooth 601 is set into the sideway, lateral resonant motion. The electrical signals can be sensed between the comb tooth electrode 601 and the electrodes 630 and 631 using the signal amplifiers 652 and/or 653 and/or 655 and the corresponding detection circuitry 662, 663 and 665 respectively. When the ligand 610 of mass $m_1$ is added on the resonating beam 601, the resonant frequency of the plate decreases by $\Delta f_1$. When the same ligand 611 is adsorbed/reacted at the different location on the central plate that did not have any ligands adsorbed/reacted yet, the resonant frequency of the beam will decrease by the same frequency shift $\Delta f_1$. It does not matter where the ligand is adsorbed/reacted on the electrostatic plate.

When the surface of the bridge or cantilever has been functionalized so that only one type of specific receptor is adsorbed or reacted on the bridge or cantilever surface, then the concentration of ligand in the environment can be calculated from the observed time dependence of adsorption or reaction and the rate of the flow of gaseous or liquid material containing these ligands.

When the different ligand 612 of mass $m_2$ is adsorbed/reacted on the plate 601 which does not contain any adsorbed/reacted species, then the resonant frequency of the plate decreases by $\Delta f_2$. When the sensing system has the sensitivity to resolve the difference between the frequencies Δf₁ and Δf₂, then different ligands $m_1$ and $m_2$ can be detected and resolved with the single sensor. The multiple ligands $m_i$ can be detected with the single sensor as long as the ligands physically adsorb on or chemically react with the material on the central plate and $\Delta f_i$ is resolved by the sensing electronics.

Figure 7A:
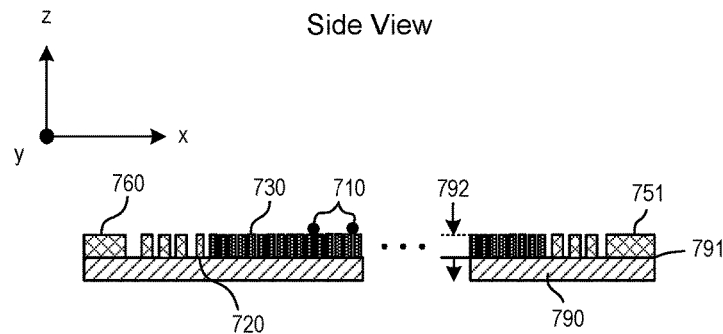
FIG. 7a is a side view and FIG. 7b is a top view of the single element electrostatic comb nanosensor with movable and stationary sensing combs, separate parallel plate driving electrodes and driving and sensing circuits.
Figure 7B:
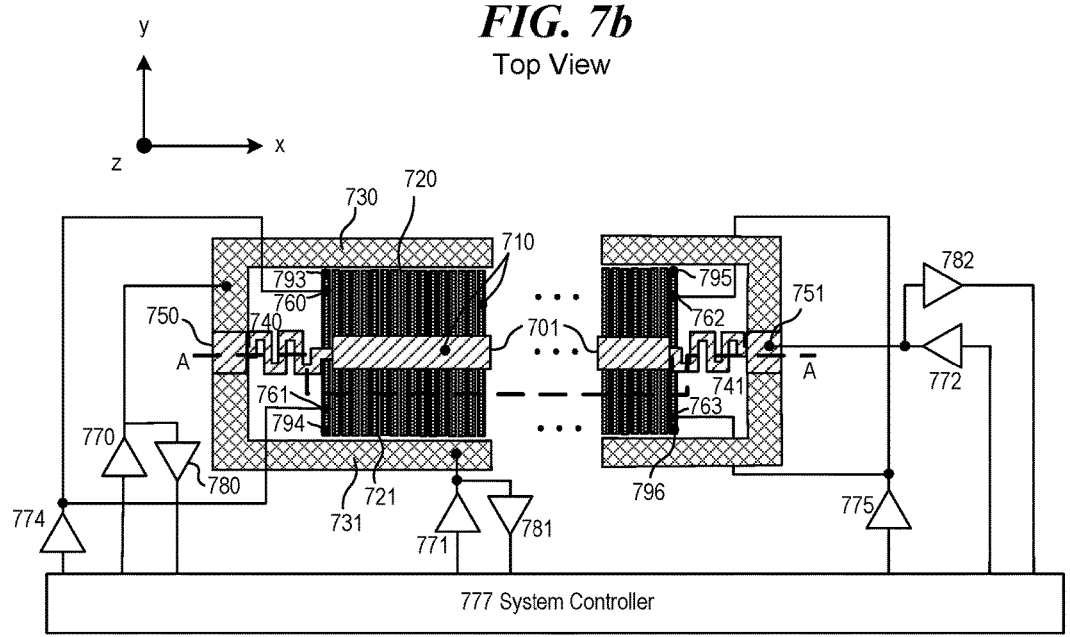

The sensitivity of the electrostatic comb sensor can be increased by adding additional teeth to the movable and the static parts of the comb sensor and by separating the driving and sensing parts of the device to reduce the noise. The schematic diagram of such sensors is presented in FIGS. 7a-b and 7c-d. The sensor in FIG. 7a-b consists of movable central plate 701 that has movable teeth 720 and 721 attached to it. The static teeth 730 and 731 interdigitate the movable teeth 720 and 721 with very small gaps between them. The complete movable structure is connected by the hinges 740 and 741 to the posts 750 and 751 respectively that reside on the substrate 790. The posts 750 and 751 are isolated electrically from the static teeth 730 and 731 and from the substrate 790. When the substrate 790 is not completely electrically insulating, the dielectric layer 791 is added between the substrate 790 and posts 750 and 751. In addition, the stationary teeth that are physically residing on the substrate 790 are electrically isolated from the substrate 790 by the same dielectric isolation layer 791. In addition, the driving teeth can be separated from sensing teeth for increased sensitivity of detection in case of in-plane x-y motion. In such a case, the outside stationary teeth 760, 761 are electrically separated from the second set of stationary teeth 762 and 763 and these teeth are also electrically separated from the rest of stationary teeth 730 and 731.

The electric voltage waveforms are applied between the movable teeth 720 or 721, and the stationary teeth 730 or 731 respectively. The driving amplifiers 770 or 771 or 772 are controlled by the system controller 777 fabricated with CMOS. This way, the moving structure 701+720+721 can be set into vibrations in y direction when the driving waveform is oscillatory. The sensing is performed by using the signal generated between the movable teeth 720+721 and the stationary teeth 730 or 731 and amplifying the signals with the amplifiers 780 or 781 or 782 and processed with the system controller 777.

Alternatively, the movable structure 701+720+721 can be set into vibrational motion in x direction by applying the driving signals between the driving electrodes 760+761 and teeth 720+721 using the driving amplifier 774. The sensing signals between the movable teeth 720+721 and stationary teeth 730+731 are amplified with sensing amplifiers 780 or 781 or 782 and processed with the system controller 777. Similarly, the driving signals can be applied between the driving electrodes 762+763 and teeth 720+721 using the driving amplifier 775 and the sensing signals are again obtained between movable and stationary teeth. When the driving waveform is bipolar and the movable structure oscillates between positive and negative x directions, the sensing signals are increased by about a factor of two compared with unipolar driving. The driving and sensing circuitries can be electrically separated and consequently, the noise level is lowered and the detection sensitivity increased.

The sensing and driving circuits can be electrically connected to the comb device so that the movable comb structures are forced to move in out-of-plane direction, z, with respect to the stationary combs, instead of lateral x or y directions described above. In such cases, the stationary teeth 760, 761, 762 and 763 can be electrically connected with the rest of the stationary teeth 730+731. The movable teeth are displaced with respect to stationary teeth in the z direction which is normal to the substrate in order to create the fringing field between stationary and movable teeth and allow initial motion in the z direction normal to the substrate. In the extreme case, the z displacement between stationary and movable teeth can be equal to the height of the movable teeth, 792. These variants for out-of-plane comb resonant motion can be accommodated by the fabrications that build stationary and movable combs in the same plane with slight z offset for these two sets of combs or in two totally different z planes.

The adsorption/reaction of ligands m, marked as 710, residing anywhere on the movable structure 701+720+721 leads to decrease of the resonant frequency by $\Delta f_1$. The frequency changes can be detected with the larger signal to noise ratio in this comb sensor 700 with the large number of movable teeth because of the large capacitance between the static and movable teeth compared with the one movable teeth structure in FIG. 6.

When high driving voltages are applied between the movable and stationary parts of the sensor, the movable portion can become unstable and displace so far that the electrical contact occurs between the movable and stationary parts of the structure, leading to the electrical short. In order to prevent such an occurrence, the mechanical stops 793, 794, 795 and 796 are placed outside of two or four corners of the movable teeth at the distance equal to about half of the gap between the movable and stationary teeth. When the movable structure is displaced by driving voltages about half of the gap, the mechanical stops 793 to 796 prevent the movable section to go any further and electrical short between the movable and stationary teeth is prevented. Normally, these mechanical stops will have the same potential applied to them as the potential of the movable teeth. The mechanical stops can be connected to the system electronics 777 and used to detect the mechanical and electrical contact between the movable teeth and the mechanical stops 793-796 and subsequently used to calibrate or optimize the driving waveforms.

Figure 7C:
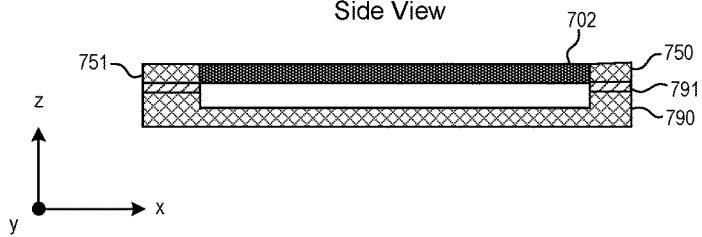
FIG. 7c is a side view and FIG. 7d is a top view of the single element electrostatic comb nanosensor with movable and stationary sensing combs, separate movable and stationary driving combs and driving and sensing circuits.
Figure 7D:
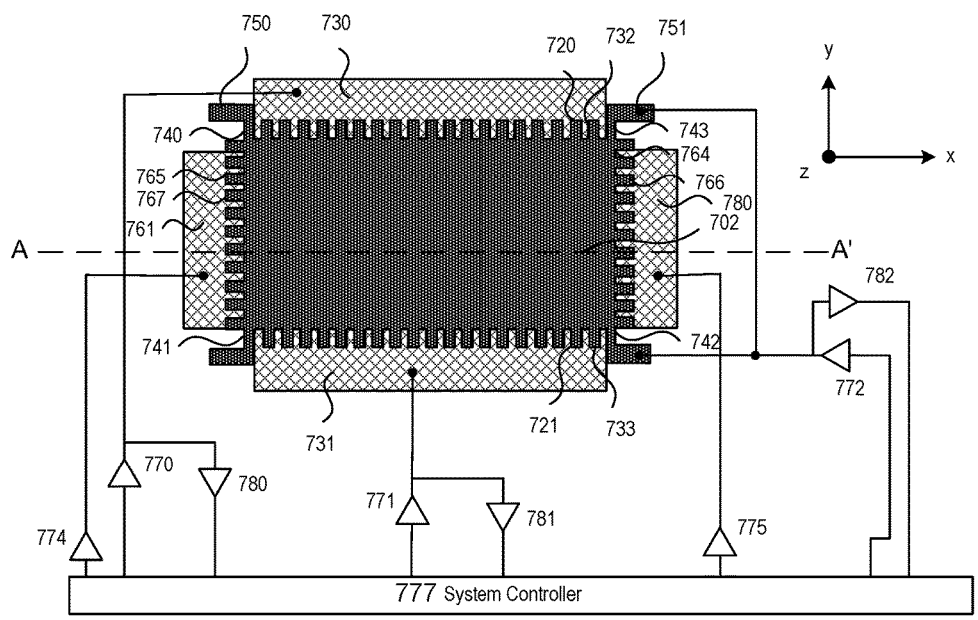

Preferred embodiment of electrostatic comb resonator is shown in FIG. 7c and FIG. 7d with side and top view respectively. The components in FIG. 7d marked with the same numbers as the components in FIG. 7b have the same functionality described above. The mechanical stops 793-796 are omitted in the resonator in FIG. 7d for clarity, but they are included in the device. The resonator presented in FIG. 7c-d has important modifications of the driving electrodes and hinges compared with the resonator in FIG. 7a-b. Instead of single tooth electrode driving geometry, the movable, driving combs 766 and 767 are placed on the movable plate 702 and the corresponding stationary, driving combs 764 and 765 are substituted for the driving electrodes 760-763. The same driving potentials are applied at the same time to both driving electrodes 760 and 761 versus the movable plate 702. More efficient driving of the resonator with lower driving voltages and power is enabled with driving combs than with single tooth driving. The preferred driving motion is in positive and negative x direction. In addition, four hinges 740-743 provide resonating bridge-like geometry that is very stable with respect to undesirable rotational and twisting vibrations that are characteristic of standard electrostatic comb actuations.

The electrical CMOS circuits 770-775, 780-782 and 777 are shown adjacent to the resonator in FIG. 7, but it is preferable to place them below or in the close proximity of the resonator to minimize parasitics and noise pick up and thus maximize signal to noise ratio and the sensitivity. This architecture applies to the sensors in FIG. 7a-b and FIG. 7-d and is expanded on below.

The resonator structures in FIG. 5-7 are electrostatically driven and sensed, and therefore they are formed using electrically conducting materials, either metals or doped semiconductors. They can be formed by the single conductive layer or composite multilayers and can be coated with thin, electrically non-conductive films that can be chosen to allow convenient attachment of receptors, referred hereto as functionalization. This functionalization can be performed on electrically conducting or non-conducting surfaces. One example of such a coating is Atomic Layer Deposition (ALD) that provides a nearly perfect monolayer or multilayer coverage with excellent conformal coatings, without significantly adding to the mass of the resonating sensor. This type of surface treatment or deposition applies to all sensing surfaces described here.

Figure 8A:
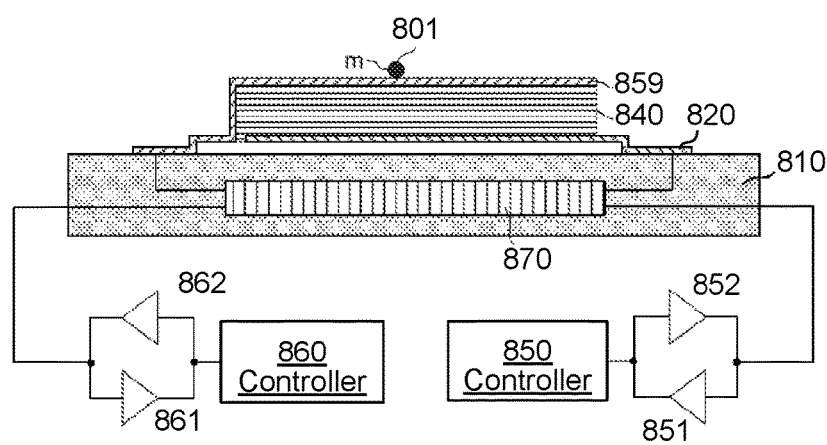
FIG. 8a depicts a side view and FIG. 8b depicts a top view of piezoelectric nanosensor and driving and sensing circuitry.
Figure 8B:
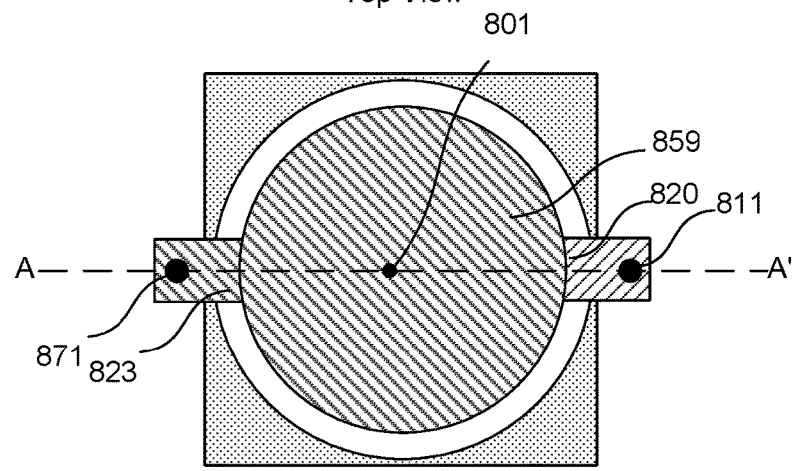

When sensing at high frequencies is preferable, the sensors based on piezo-electric resonators can be used. The side view of the piezo resonator is shown in FIG. 8a and the top view in FIG. 8b. The resonator consists of piezoelectric layer 840 that is surrounded by two electrodes 820 and 8509. The resonating structure resides above the cavity and is suspended by two bridges 822 and 823. The applied voltage waveform is applied to the electrodes 820 and 8509 from the driving amplifiers 852 and/or 862 that are driven by the driving circuits included in the electrical circuits 850 and/or 860. As a result of applied voltage across the piezoelectric layer 840, the material will undergo in-plane or out-of-plane expansion or shrinkage. The driving voltage at frequencies that correspond to the mechanical resonances of the structure will result in maximum resonant response amplified by the sensing amplifiers 851 and/or 861 and detected by the sensing circuits included in the electrical circuits 850 and/or 860. The addition of mass 801 leads to change of resonant response by shift to lower resonance frequency and phase change.

The CMOS circuit 870 is connected to the electrodes by vias 811 and 871 formed during monolithic fabrication of CMOS and NEMS or by electrical interconnects 811 and 871 formed during bonding of CMOS and NEMS wafers described below.

The resonant frequencies of the piezoelectric sensor can typically be in 1 to 30 GHz range. When the mass 801 is added to the resonator, its resonant frequency will shift downward and the mass of the adsorbed or reacted species can be determined. The resolution of the sensors depends on the broadening of the resonant peaks compared with the resonant frequency itself. The overall broadening of resonance is the result of internal energy losses of the resonant structure and external loss effects from damping of viscous media surrounding the resonator. The effect of viscous media damping decreases with increasing resonant frequency. The electrostatic resonators have typical resonant frequencies in 1 MHz to 1 GHz range. Consequently, the broadening of the piezoelectric resonant peaks due to external damping is much lower than the broadening of the resonant response of electrostatic sensors relative to their resonant frequencies. The damping effects and resonant broadening can be further reduced by employing lateral resonant motion in x-y plane shown in FIG. 8 and control of environment surrounding the resonator described below.

Figure 9A:
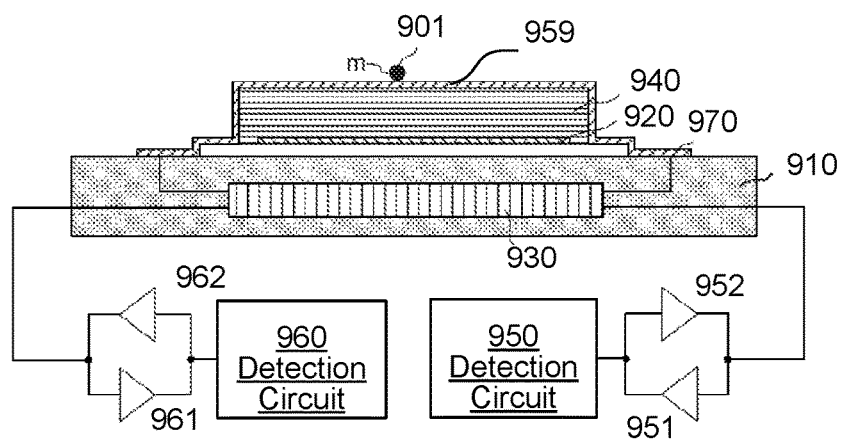
FIG. 9a shows a side view and FIG. 9b shows a top view of the single element piezoelectric nanosensor suspended with tethers and driving and sensing circuitry.
Figure 9B:
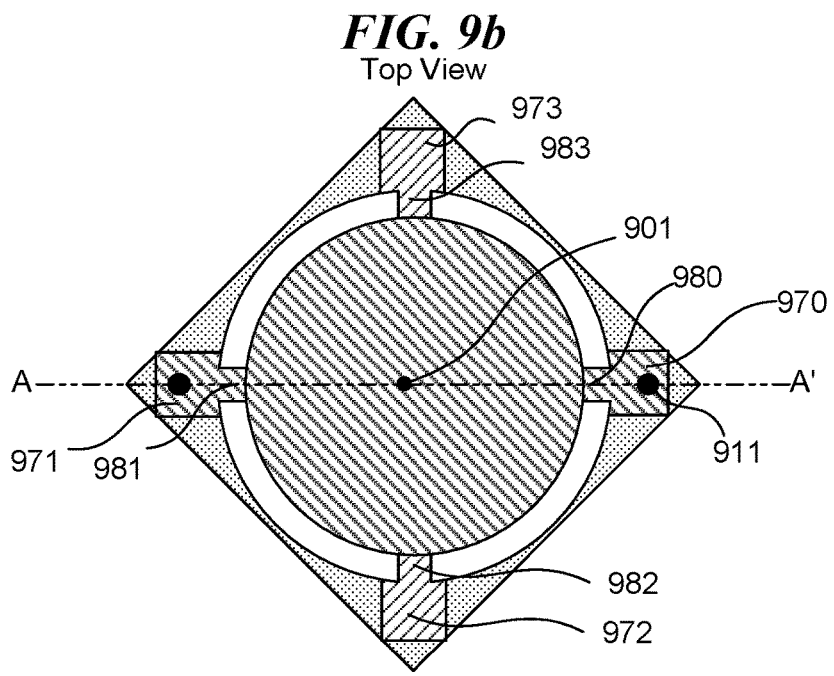

Another embodiment of the piezoelectric sensor is shown in FIG. 9a-b. The basic operational principle is the same as for the resonator in FIG. 8. The resonating structure defined by the piezoelectric layer 940 and two electrodes 920 and 9509 is suspended above the substrate 910 by four tethers 980-983. The electrical driving signal is supplied to the resonant structure through the electrical pads 970-973 and vias 911 that connect the electrodes 920 and 959 to the CMOS circuit 9730. The driving voltage waveforms are supplied by the driving circuits included in the electrical circuits 950 and/or 960 and the driving amplifiers 952 and/or 962. The adsorption or reaction of mass 901 with the sensor surface or the receptors residing on the surface is detected by the frequency shift of the resonating structure using the sensing amplifiers 951 and/or 961 and the sensing circuits included in the electrical circuits 950 and/or 960.

Even though the electrical driving and sensing circuits in 950 and 960 and driving amplifiers 952 and 962 and sensing amplifiers 951 and 961 are shown for clarity separately from control circuit 930, it is preferable to incorporate them within CMOS circuit under or in close proximity of the resonator to minimize parasitics and noise pick up and thus maximize signal to noise ratio and the sensitivity. This architecture applies to the sensors in FIG. 8, in FIG. 9a-b and FIG. 9c-d outlined below.

The energy losses of the piezoelectric resonators or the broadening of resonant peaks can be reduced by the selection of piezoelectric material, by control of its microstructure during deposition, by the selection of electrode materials and control of the piezoelectric-electrode interfaces. When the electrodes do not reside directly on the piezoelectric surfaces but are spaced by air or vacuum gap, the broadening of the resonant peaks can be further reduced. The different resonant modes can be excited with the external driving voltage waveforms. The lateral breathing modes with in-plane motion have typically lower resonant losses than the motion in the direction normal to the plane of the resonator. The poling of the piezo materials with the large external field sets the direction of the permanent electric field and allows control of the specific resonances. The electric field poling can be performed at elevated temperatures and at high electric fields.

In order to keep very high sensitivity of the piezoelectric sensors and at the same time achieve very high resonant frequencies, the mass of the resonant plate should be minimized while imparting high stiffness to the suspending tethers. This can be accomplished by keeping the area and thickness of the piezoelectric layer small and by decoupling of the electrode thickness and tether thickness or by adding another layer to tethers. This modification of the vibrating structure will increase the complexity of the sensor and its fabrication somewhat by adding a deposition, lithography and etching steps, but it will result in improved performance.

Figure 9C:
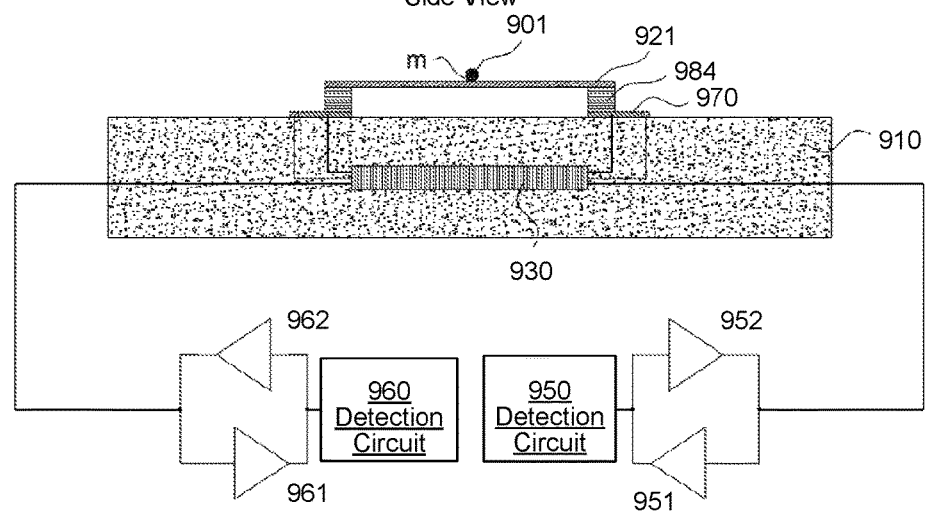
FIG. 9c shows a side view and FIG. 9d shows a top view of the single element piezoelectric nanosensor with hinges having the piezoelectric driving and sensing functionality.
Figure 9D:
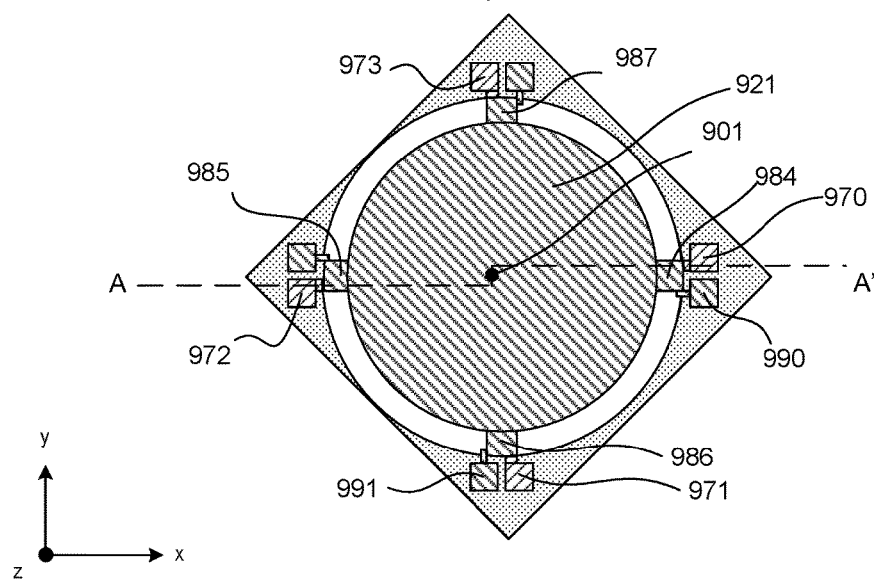

The piezoelectric resonators that do not have dependence of resonance frequency on the position of the added mass 901 can be realized by using a plate 921 suspended above the substrate 910 on piezoelectric layer 940 limited to supports 980-983, as shown in FIG. 9c-d. The plate 921 has at least a receptor attached to it.

The piezoelectric devices 980-983 consist of the piezoelectric layer 940 placed between an electrode 925 residing on the substrate 910 and the plate 921 that serves as another electrode. The application of electric voltage to the devices results in piezoelectric layer 940 expansion and shrinkage in z direction or shear displacement in x or y direction, leading to the translational displacement of the electrode plate 921. The addition of mass 901 leads to change of resonant response by shift to lower resonance frequency and by phase change, as detected by the sensing circuits in 950 and 960.

The driving electrical pads such as 970 are connected to the electrodes 925 of the piezoelectric layer 940 and the driving electrical pads such as 990 are connected to the electrode plates 921. The sensing electrical pads such as 971 and 991 form connect to two electrodes having the piezoelectric layer 940 between them. In another embodiment, the same piezoelectric devices can be used both as driving and sensing elements. The number of the driving and sensing structures in FIG. 9c-d is only illustrative of the actual number, as it can vary from one to many.

In order to detect the specific agents sensitively, the large array of sensors can be built. When there are N sensors built into the sensing system, the signal to noise ratio is improved by √N. In one implementation, each sensor has its own detection circuit associated with it. In such a case, the parasitic signals and noise pick ups are minimized and the best detection sensitivity is achieved. The driving circuits can drive multiple resonators or single resonators.

Figure 10:
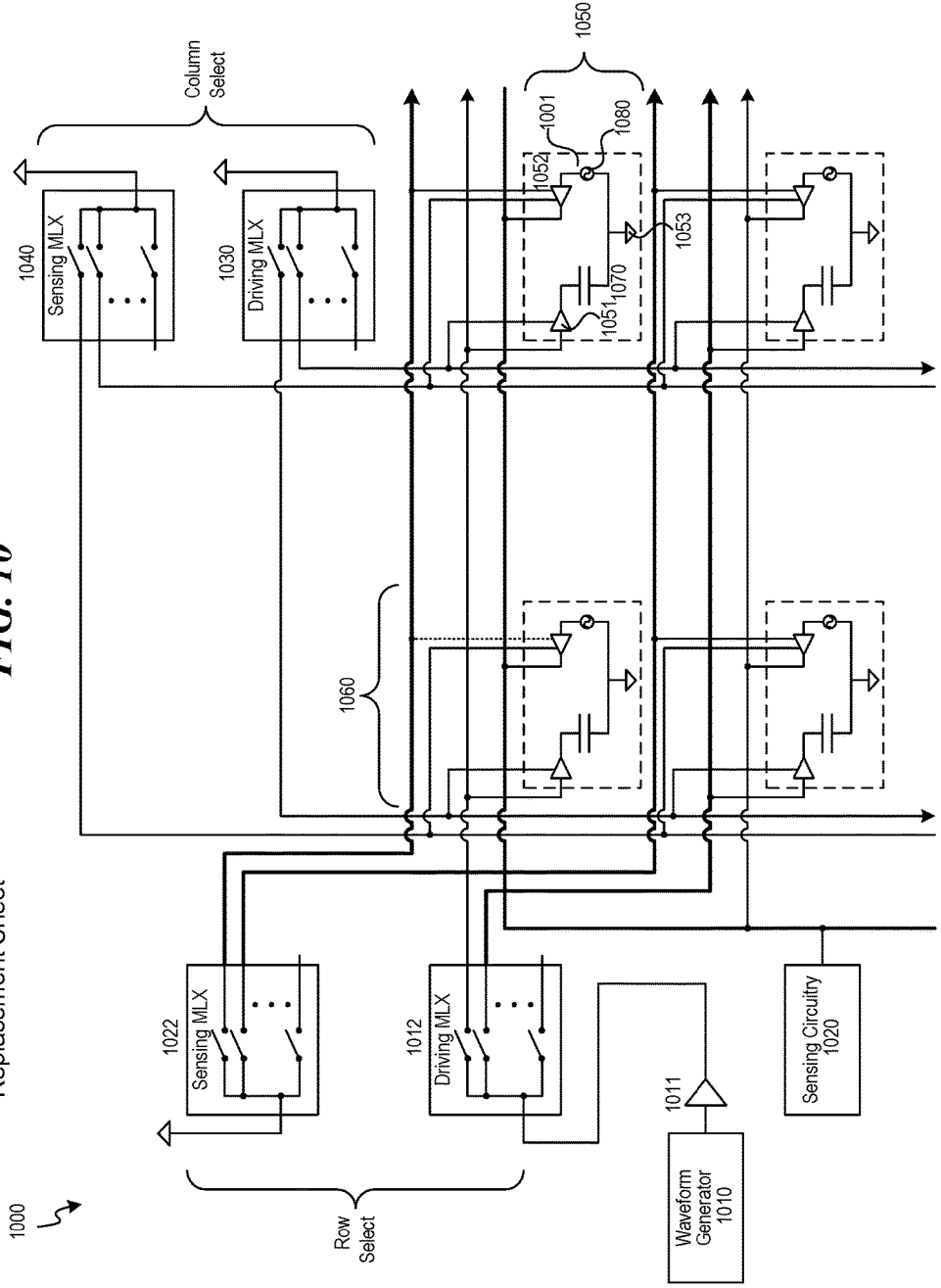
FIG. 10 is a schematic diagram of the two dimensional array of nanosensors with single driving circuit and single detection circuit supporting multiple sensors.

When the detection circuit occupies larger area than the area occupied by a resonators, one detection circuits can serve multiple resonators as shown schematically in FIG. 10.

In order to detect the specific agents sensitively, the large array of sensors can be built. Multiple sensors can be used to improve the signal to noise ratio and measurement sensitivity and accuracy. FIG. 10 shows a high level schematic representation of the detection circuit for electrostatic or piezoelectric sensors. The sensors 1001 are arranged in the x-y matrix with the rows 1050 and columns 1060. The driving element of the sensor 1001 is represented by amplifier 1051 and capacitor 1070. The sensing element of the sensor 1001 for a frequency measurement of the moving element is depicted by an amplifier 1052 and detector 1080. The driving element 1051+1070 and the sensing element 1052+1080 share a common potential 1053. In this schematic, the voltage is represented as a ground symbol but the actual voltage potential will be based on various system design parameters. The drive amplifier 1051 is shown with an enable signal on corresponding driving column select multiplexer 1030 and the driving row select multiplexer 1012 to selectively enable the waveform on the driving element of a given sensor. The sense amplifier 1052 is shown with an enable signal on corresponding sensing column select multiplexer 1040 and the sensing row select multiplexer 1022 to selectively enable the sensing signal of a given sensor to be read by the sensing circuitry 1020. There are numerous ways to connect multiple sensors and multiplex the driving and sensing signals. It is possible to drive multiple sensors simultaneously or sequentially and to sense the outputs simultaneously or sequentially. The whole x-y matrix of sensors can be also subdivided into blocks in which one sensor in each block is driven and monitored simultaneously, thus reducing mechanical and electrical coupling between neighboring sensors and reducing power requirements at the same time. Increased accuracy can be achieved by driving multiple sensors and selectively enabling various groups of sense outputs. This schematic is used to demonstrate the basic principle of matrix driving and sensing and does not necessarily represent the preferred embodiment. As an example, the sensing signals could be also measured through Radio Frequency (RF) means without the need for the matrix of x-y wires.

Measuring the frequency of the vibrating electrostatic or piezoelectric elements of the NEMS device has a number of advantages including the ability to mix and/or compare a large number of sensors simultaneously without frequency matching errors from multiple RC oscillators. The oscillator signals from the multiple sensors can be combined and the desired frequencies extracted through digital signal processing means.

The principle of detection of adsorbed/reacted mass on the sensor is the same as described earlier for the electrostatic bridge, cantilever or comb sensor.

Next, the fabrication process and materials for NEMS sensor devices of bridge, cantilever or comb type will be described, even though description will be given with particular emphasis on the multi-teeth comb sensors illustrated in FIG. 7.

Figure 11A:
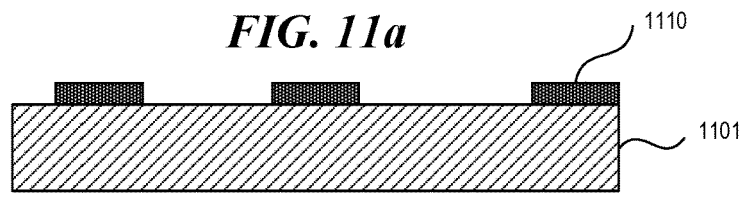
FIG. 11a to FIG. 11g represent outline of the fabrication process for electrostatic nanosensors using separate fabrication of CMOS and NEMS wafers and wafer level bonding of CMOS and NEMS wafers.

The fabrication process starts with the substrate 1001, typically silicon as shown schematically in FIG. 11a. Alternatively, other substrates such as glass, that permit less expensive fabrication, can be used. In such a case, the fabrication can be performed on large glass plates such as those used in the plant used for thin film transistor (TFT), liquid crystal displays (LCD) manufacturing. It is likely that such a fabrication process would be less expensive than one done in the CMOS facility, but the device dimensions will be larger in the LCD fab than CMOS fab due to photolithographic equipment with lower spatial resolution in LCD fab.

Figure 11B:
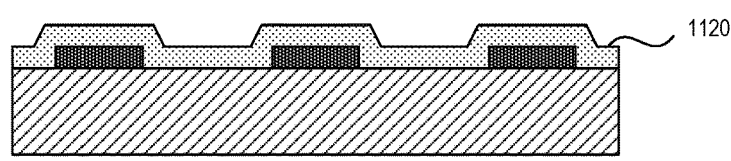
Figure 11C:
Figure 11D:
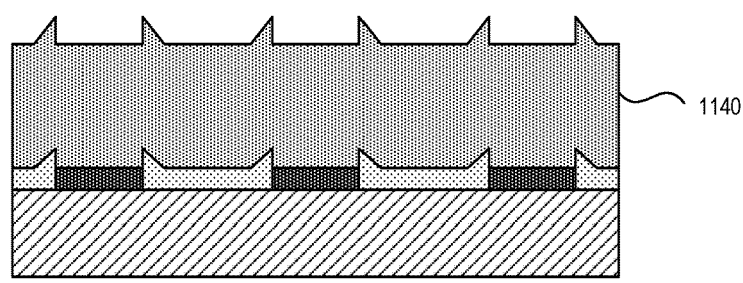
Figure 11E:
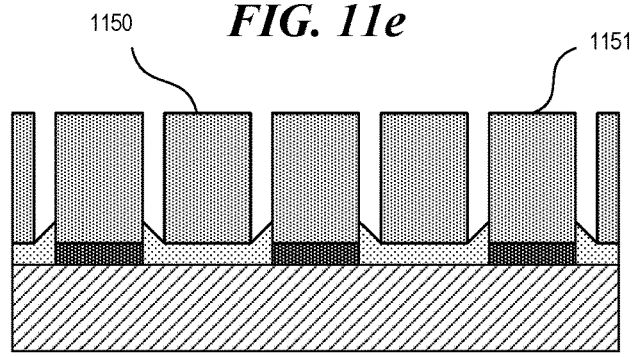
Figure 11F:
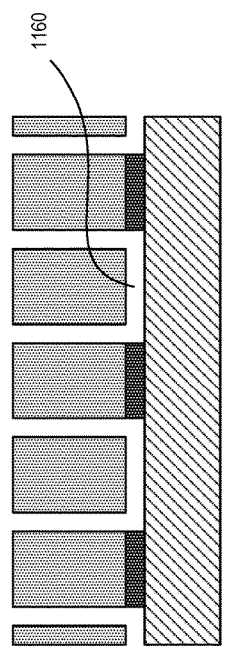

The thin film of electrically insulating material, such as silicon dioxide, silicon nitride, aluminum oxide, etc. is deposited on the substrate 1101 and patterned in places where the static teeth 1151 of the comb sensor will be attached to the substrate 1101. The dielectric islands supporting future static teeth are labeled as 1110 in FIG. 11a. The following step in FIG. 11b involves deposition of sacrificial film 1120 that will be removed at the end of fabrication of the structure. The materials that can be used as sacrificial material include photoresist, amorphous carbon, silicon dioxide, silicon nitride, etc. The material 1110 supporting future stationary teeth and sacrificial material 1120 have to be dissimilar, so that etching of the sacrificial material 1120 later on will not affect the attachment layer 1110. As an example, when silicon nitride is used as the attachment film 1110, silicon oxide or amorphous carbon can be used as sacrificial material 1120 and vice versa. The sacrificial material 1120 is patterned as indicated in FIG. 11c, creating islands 1130. The following step in FIG. 11d involves deposition of the structural material 1140 for definition of stationary and movable combs, hinges and posts of the structure in FIG. 7. The examples of electrically conducting structural materials are doped polysilicon, doped silicon-germanium, aluminum alloys, including AlTi and AlTiN and other metallic alloys. The next step in FIG. 11e proceeds with patterning and etching of structural material 1140 to form the movable teeth 1150 and stationary teeth 1151 and other structures. The final step of NEMS fabrication shown in FIG. 11f involves removal of sacrificial material 1130 to form cavities 1160 underneath the teeth 1150 to free them so that they can move. When the sacrificial material is photoresist or carbon, dry ashing in oxygen can remove these sacrificial materials effectively. When the sacrificial materials are silicon dioxide, silicon nitride, etc., the dry etching of these materials, vapor release or wet etching followed by critical point drying can be used. The further steps include formation of bonding pads with the right bonding materials, optional deposition of sealing material on resonator substrate and functionalization of the NEMS structure.

Figure 11G:
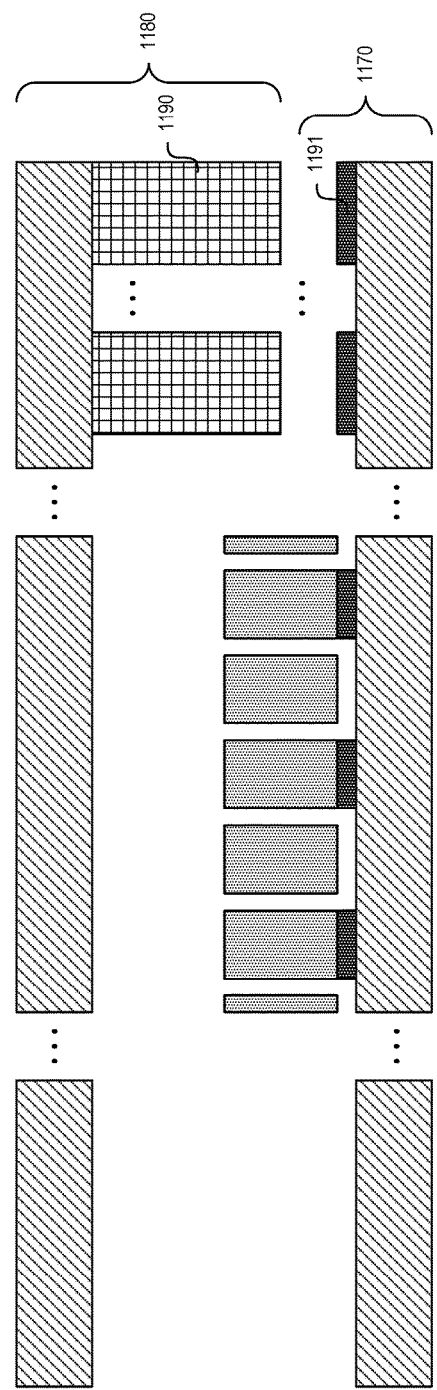

The NEMS structure can be built monolithically on CMOS with the sensing and driving circuits and then further processing involves forming the sensing cavities and functionalization of the resonators. When the NEMS and CMOS are fabricated on the separate wafers 1170 and 1180 respectively, the formation of electrical bonds between two wafers and sealing of sensing chambers can be performed at the same time as schematically indicated in FIG. 11g. The bonding structure/materials 1190 and 1191 can be patterned or deposited onto CMOS or NEMS wafers or onto both wafers.

The fabrication of the piezoelectric resonator starts with the deposition of sacrificial layer 1215 on the substrate 1210 such as single crystal silicon or glass which contains electrical metal lines 1202 and 1203 connecting to CMOS circuit or vias to the underlying CMOS circuit, as schematically outlined in FIG. 12a. The sacrificial material 1215 can be silicon dioxide, silicon nitride, amorphous carbon, amorphous silicon, metal or photoresist, depending on the other structural materials in the structure. At the end of the fabrication of the piezoelectric stack, the sacrificial material is removed without altering the resonant actuator. The amorphous carbon as a sacrificial material offers several advantages because it can be deposited by simple plasma enhanced chemical deposition process at wide range of deposition temperatures, at relatively high deposition rates, it is relatively inert during subsequent processing and can be removed easily and at high rate by dry ashing in oxygen. Amorphous carbon as sacrificial material also permits wet cleaning steps that are often desirable in order to remove etching residues. Photoresist as sacrificial material does not allow these wet cleaning steps. Another standard sacrificial material is silicon dioxide that can be deposited by plasma enhanced deposition techniques at temperatures below 400 C and can be removed by dry etching using fluorinated gases or by vapor hydrofluoric acid or by wet etching in hydrofluoric acid followed be critical point drying.

Next, the sacrificial layer 1215 is patterned with photoresist and etched to open regions 1216 where the electrodes will be attached, as shown in FIG. 12b. In the next step in FIG. 12c, the bottom electrode film is deposited and patterned using photolithography and etching to create stitches to the electrical and mechanical contacts in regions 1216. The following fabrication step in FIG. 12d involves deposition of piezoelectric materials 1240 such as aluminum nitride AlN, zinc oxide ZnO or lead zirconate titanate $PbZrTiO_3$. AlN and ZnO or $PbZrTiO_3$ can be deposited by rf sputtering and $PbZrTiO_3$ can be also deposited by repeated spin coating and sintering of multiple layers. The piezoelectric film is also patterned with photoresist and etched to define the resonating structure. The common etchant for AlN, ZnO and $PbZrTiO_3$ are used. The final deposition layer in FIG. 12e is the top electrode 1250 that is deposited with somewhat conformal coating that covers walls of the piezoelectric film and brings the top electrode down to the stitch 1220. In order to make this wall coverage easier, the piezoelectric film 1240 can be deliberately etched with less anisotropic process that produces angled walls.

After the piezoelectric layers are deposited or after they are patterned, the piezoelectric material can be poled by setting the wafer into the high electric field at elevated temperatures. This process aligns the domains of different polarization and can improve the effectiveness of the piezoelectric material so that the displacements are increased compared with the unpoled material for a given values of electric field. The final step of fabrication of the piezoelectric actuator in FIG. 12f is the removal of sacrificial material 1215 to release the resonating structure.

Next, a number of exemplary applications for the single molecule sensing is described below.

Figure 13A:
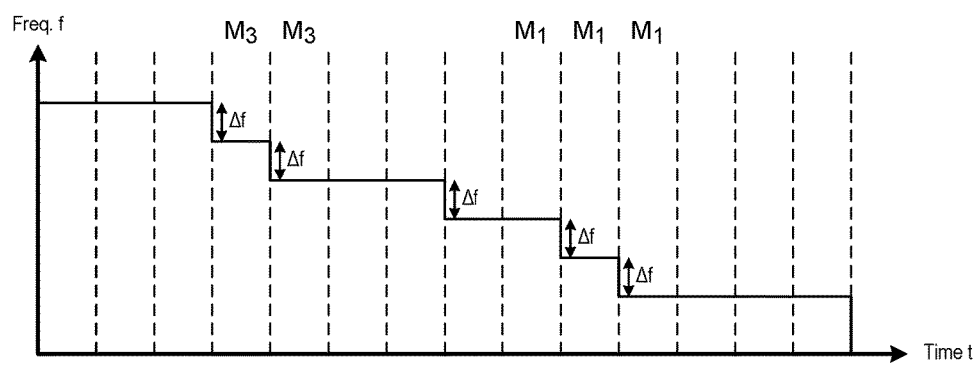
FIG. 13a to FIG. 13b are examples of detected signals obtained from sensing circuit for detection of the single species and simultaneous detection of multiple species, respectively.
Figure 13B:
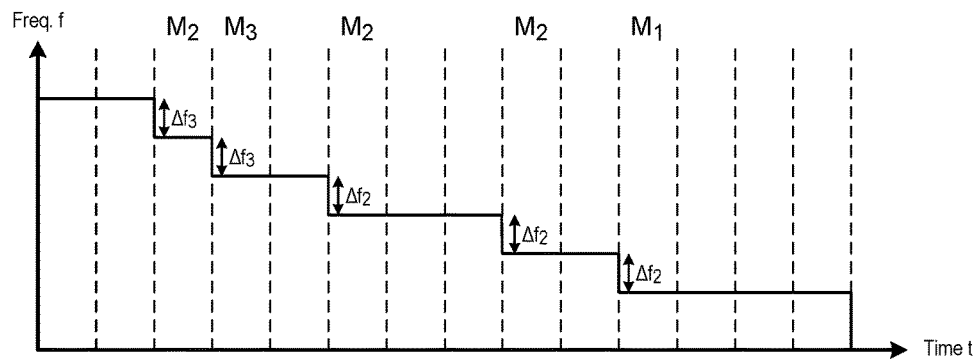
Figure 14A:
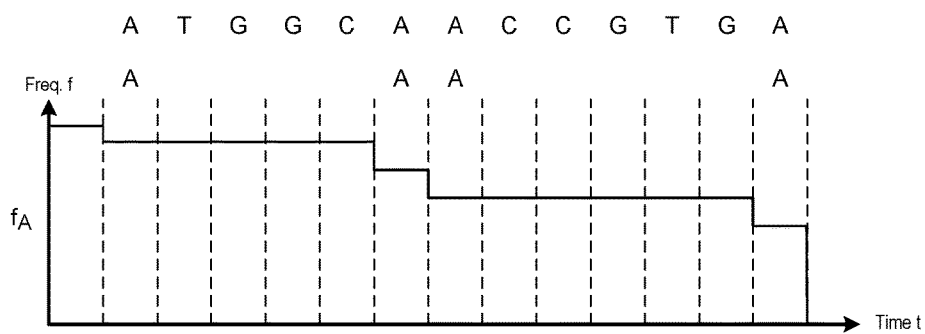
FIG. 14a to FIG. 14d are examples of detected signals obtained from sensing circuitry for DNA (deoxyribonucleic acid) sequencing in four detection channels.
Figure 14B:
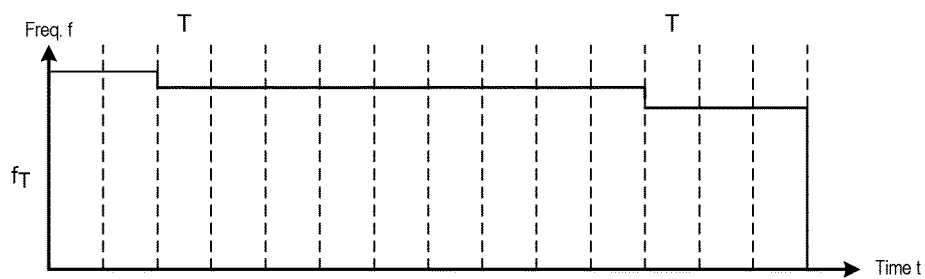
Figure 14C:
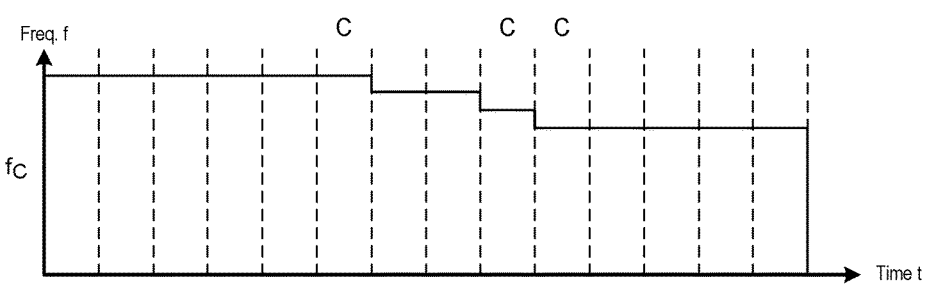
Figure 14D:
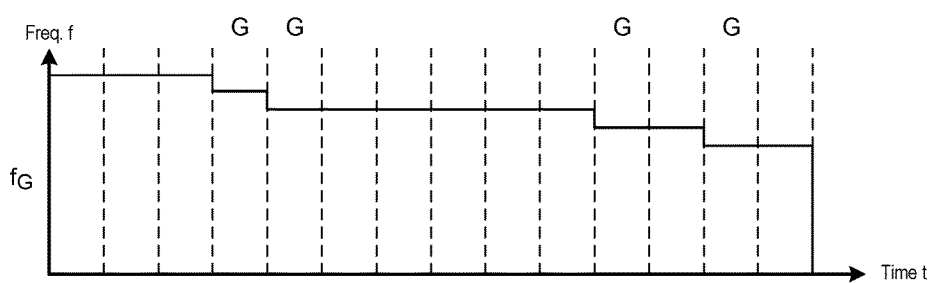

In the first embodiment, receptors are placed on the sensor in specific locations or globally. Ligands are then introduced, suspended in the fluid, either gas or liquid, and allowed to interact with the receptors. When adsorption or reaction occurs, the mass of the sensor is increased and the frequency decrease is detected. The typical detected signal is illustrated in FIG. 13a where the frequency, f, is plotted as a function of time, t. Each frequency decrease by $\Delta f$ corresponds to physical adsorption or chemical reaction of a single molecule of ligand. The multiple ligand molecules can also be detected. The number of ligands detected over a given period of time represents concentration of ligands in the contact medium. In another example, multiple species with different molecular weights $m_i$, but with the same or similar terminal group interact with the same, specific receptors on the sensor. The corresponding time dependence of frequency is shown in FIG. 13b. The frequency decreases by $\Delta f_1, \Delta f_2, \ldots \Delta f_i, \ldots \Delta f_n$ as a function of time. The frequency changes of $\Delta f_i$ correspond to attachment of ligands with molecular weight $m_i$. If the species are separated by gas or liquid chromatography or other methods according to increasing molecular weight, then the decreases of resonant frequency will be progressively larger.

Binding interaction of the ligands extracted from the tested sample to receptors placed on the sensor has to be immune from common interferants. The physical adsorption or chemical reaction has to be specific to the combination of receptors and ligands. In addition, the probability of the interaction or reaction should be as high as possible so that the sensitivity is high.

In another example that represents deoxyribonucleic acid (DNA) sequencing, the detected signals are shown in FIG. 14. The nano mass spectrometry described here represents the back end of DNA sequencing process. In the conventional DNA sequencing, DNA is unwound into two individual strands, then split into four samples in which each of them is treated with specific reagents that break the molecules into fragment ending with A or T or C or G bases. Subsequently, these four sets of fragments are sorted out according to their size by flow electrophoresis in four parallel channels. The fragments are visualized with phosphorescent or X ray labels in four separate channels and ordered by their superposition according to their positions on the electrophoretic plate, thus yielding the actual sequence. The described nano mass spectrometer with four separate channels is added to the output of size separated ligands with A, T C and G terminated fragments. Nano mass spectrometer detects these ligands as a function of time in four channels in parallel, as indicated in FIG. 14a-d for neucleotides A, T, C and G respectively. The detected mass increases at specific times define the order of individual bases as shown in FIG. 14. The resulting reconstructed DNA sequence is shown at the top of FIG. 14.

In the alternate embodiment, the ligands are placed either globally or in specific locations on the sensor and the receptors are introduced in the liquid phase. The same physical adsorption or chemical reaction as above can occur and if it does, the mass of the sensor is increased and detected.

Figure 15A:
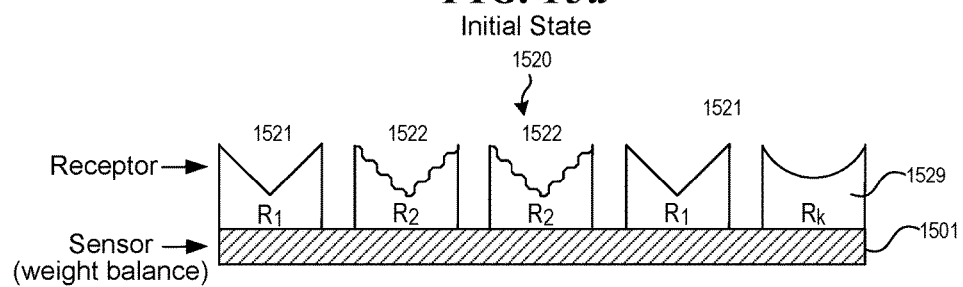
FIG. 15a to FIG. 15c are schematic diagrams of nanosensor functionalized with multiple receptors for selective detection of multiple species.
Figure 15B:
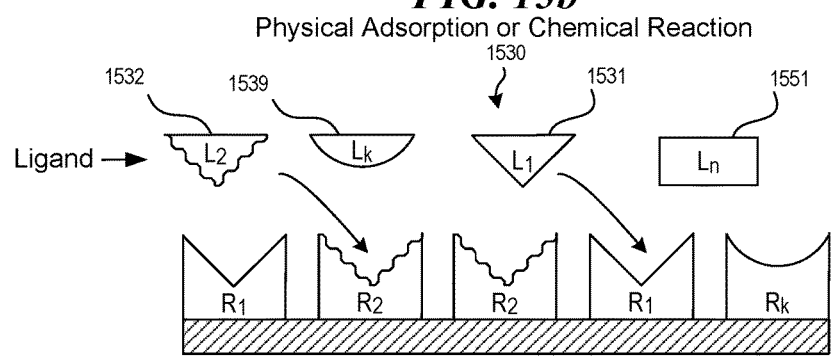
Figure 15C:
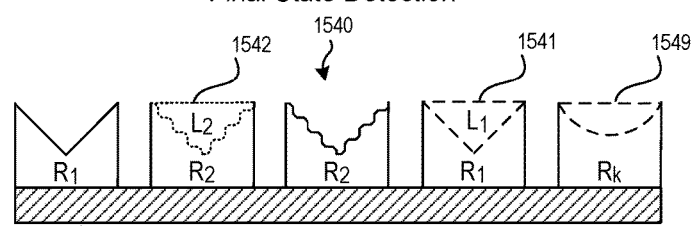

In addition, the multiple ligands can be detected by the same sensor, as shown in FIG. 15. In such a case, the multiple receptors $R_1, R_2, \ldots R_k$, labeled as 1521, 1522, ... 1529 are placed on the sensor surface 1501. The ligands $L_1, L_2, \ldots L_k$ labeled as 1531, 1532, ... 1539 are introduced either in gaseous or liquid phase and allowed to interact with respective receptors 1521, 1522, ... 1529 selectively and without interference. In addition, additional ligands, $L_n$ labeled 1551, can be present that do not interact with any receptors on the sensor surface. As a result of specific interactions by physical adsorption or chemical reactions in FIG. 15b, the corresponding ligands are attached to specific receptors. Unattached ligands can be washed away by suspending liquid in the case of detection in liquids. The suspending liquid can be removed and pressure lowered as described below. The detection of the ligands is performed in the state represented by FIG. 15c, where different frequency decreases at different times correspond to the detection of different receptors+ligands complexes 1541, 1542, . . . 1549. Certain ligands, such as $L_n$ represented by 1551 label are not detected.

In yet another embodiment, volatile organic compounds can be monitored. The monitoring of the compound can be done with the sensitive coating such as doped tin oxide, $SnO_2$ or polypyrrole. In such cases, the resistance of the coating is changed by adsorption or reaction of organic molecules on the surface of resonator, and consequently concentration of organic compound can be detected by the mass changes and by the electrical resistance changes. This hybrid mass and resistance sensor has the advantage of being more sensitive and specific than the single type of detector.

Next, several specific embodiments of applications of the above described nano mass sensors will be presented. First, two examples of cancer detection are outlined.

The detection of acute myeloid leukemia is based on binding of CD 33 transmembrane receptor or anti-CD 33 antibody (gemtuzumab; ozogamicin; Mylotarg) to the sensor and introducing a sample containing the oncogenic protein.

Similarly, detection of certain types of breast cancer can be done by fixing V-erb b2 (HER2/neu) receptor tyrosine kinase or anti-V-erb b2 antibody to the sensor to interact with trastuzumab (Herceptin).

Binding of other oncogenic proteins to their respective antibodies can be used to diagnose other forms of cancer. These include epidermal growth factor (EGF) or the EGF receptor. In addition, monitoring levels of Platelet Derived Growth Factor (PDGF), or Vascular Endothelial Growth Factor (VEGF) can be useful because of the involvement of these growth factors in proliferative disease (macular degeneration and artheriosclerosis, etc.).

Additional examples of detection with the described sensors include detection of glucose, insulin, and hemoglobin (HbA1C). For example, the prosthetic group Flavin Adenanine Diaminase (FAD) of Cyclooxigenase (Cox) is attached to the sensor surface. It is reduced by glucose yielding gluconate to reduced form of FAD—FADH2, resulting in increased mass of the sensor that is detected. This reaction is immune to common interferants such as ascorbic acid, uric acid and acetomenophen. Insulin can be detected by placing reporter enzyme —alkaline phosphatase (ALP) on the sensor and adding insulin-containing samples in combination with the ALP substrate (4-aminophenolphosphate; 4-APP). The interaction of insulin with the reporter enzyme is recorded by detection of specific, increased mass. Alternatively, insulin can be detected by interaction with anti-insulin antibodies. Also binding of blood samples to sensor-associated anti-hemoglobin antibodies can be used to identify the concentration of HbA1c without prior separation of hemoglobin from the glycated form.

Lactate, alcohol and ozone are other examples of analytes that can be detected with the above described electrostatic or piezoelectric sensors.

Another example of use of the single molecule detection is sensitive detection and differentiation between different explosive materials.

The common explosives include trinitrotoluene (TNT), pentaerythritol tetranitrate (PETN) or cyclo-1,3,5 trimethyl-ene 2,4,6 trinitramine (RDX). These explosives have vapor pressures at room temperature down to $5 \times 10^{-9}$ torr range.

The principle of detection of these explosives is again based on ligand-receptor interactions detected by the decrease of the resonant frequency of the sensor containing receptors on its surface. The receptor (antibody) for quantitative TNT detection is immunoglobulin G (IgG). In order to suppress false positives, Bovine Serum Albumin is added to IgG.

The antibody for detection of PETN or RDX is perylene or sulfonated perylene. This antibody can be placed on the sensor surface by adding the polymer binder such as polyethylene. Perylene and polyethylene can be dissolved in linear hydrocarbon solvent such as squalene ($C_{30}H_{62}$) in order to ease deposition of perylene on the sensor surface. Adhesion of perylene to the sensor surface can be improved with adhesion promoter such as 3-amino propyl trimethoxysilane.

Figure 16:
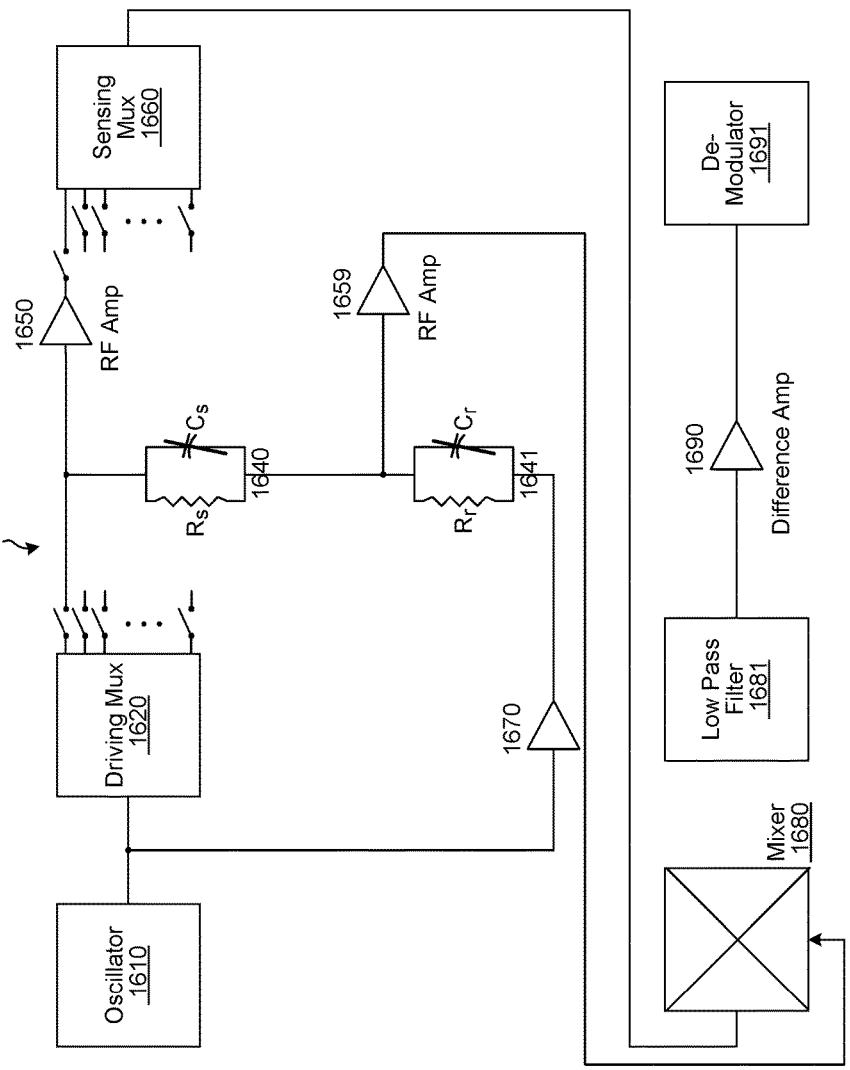
FIG. 16 is the diagram of the electrical circuit for detection of small changes of resonant frequencies.

An example of simplified electrical CMOS circuitry for detection of small changes of frequency of sample sensors is outlined in FIG. 16. The resonant structures of sample sensors 1640 and reference sensor 1641 are represented by simplified resistance-capacitance equivalent circuits, $R_s C_s$ and $R_r C_r$ respectively. The oscillator 1610 establishes the resonant frequency of the sample sensor 1640 by driving the frequency sweep and monitoring output voltages of the sample sensor, after amplification of sensor signal with amplifier 1650. The multiplexer 1620 can switch between different sensors 1640 and sensing multiplexer 1660 can switch signals from different sample sensors. The sample sensors are then normally driven at or near the resonant frequency f of the sensor. The reference sensor 1641 is driven at the same frequency from the same oscillator 1610, after inverting the oscillator signal with inverter 1670. The reference sensor signal is amplified with the amplifier 1659 and sent into mixer 1680 where it is mixed with the sample sensor signal. The described detection principle follows superheterodyne technique of detection of the amplitude or phase modulation which leads to determination of the frequency difference after passing the signal through the low pass filter 1681, the difference amplifier 1690 and demodulator 1691. The driving and sensing of the sample and reference resonators can be performed with or without multiplexing, depending on whether the circuit fits in the similar area as the resonator.

The sensed voltages of sample sensors before exposure of ligands to receptors $V_{sb}$ and reference sensor voltages $V_{rb}$ are mixed or beaten against each other, producing the signal modulated at frequency $\Delta f_b = f_{sb} - f_{rb}$, where $f_{sb}$ and $f_{rb}$ are sample and reference resonant frequencies before exposure. The same signal mixing and measurement are repeated after exposure of ligands to receptors, generating the signal modulated at frequency $\Delta f = f_{sa} - f_{ra}$, where $f_{sa}$ and $f_{ra}$ are sample and reference frequencies after exposure. The references do not change during short period of time between two measurements, thus $f_{ra} = f_{rb}$. The sample resonant frequency changed by $\Delta f = f_{sa} - f_{sb}$ as a result of increased mass by m, where $\Delta f = f_{sa} - f_{sb} = \Delta f_a - \Delta f_b$. The effective capacitance of sample sensors and reference sensors is very small, in attoFarad ($10^{-18}$) to femtoFarad ($10^{-15}$) range. For this reason, the parasitic impedances, including parasitic capacitances have to be minimized by placing the detection Complementary Metal Oxide Semiconductor (CMOS) circuitry below, above or adjacent to the electrostatic NEMS sensor in the close proximity.

It is desirable to design the resonant frequency of the sensing structure as high as possible, typically from 1 MHz to 30 GHz. The adsorption or reaction of the single ligand on the sensor is going to decrease the resonant frequency typically by 1 Hz to 1 MHz. Typical required sensitivity ranges from 1 part per thousand to 1 part per billion. The direct measurement of absolute frequencies is also possible, but it would be susceptible to error, noise and manufacturing tolerances. It would not have enough resolution or would require very long acquisition times, and for this reason, the detection based on signal mixing principle that produces signals with frequency difference and frequency sum of sample and reference signals is the preferred method.

The fabrication of the integrated sensor that contains NEMS sensor and CMOS detection circuitry can be done monolithically by fabricating CMOS and NEMS on one wafer sequentially or by electrically bonding the NEMS and CMOS wafers that were fabricated separately. The sensing chamber with the seal and input and output openings can be formed during the electrical wafer bonding step or in the separate bonding step.

Figure 17A:
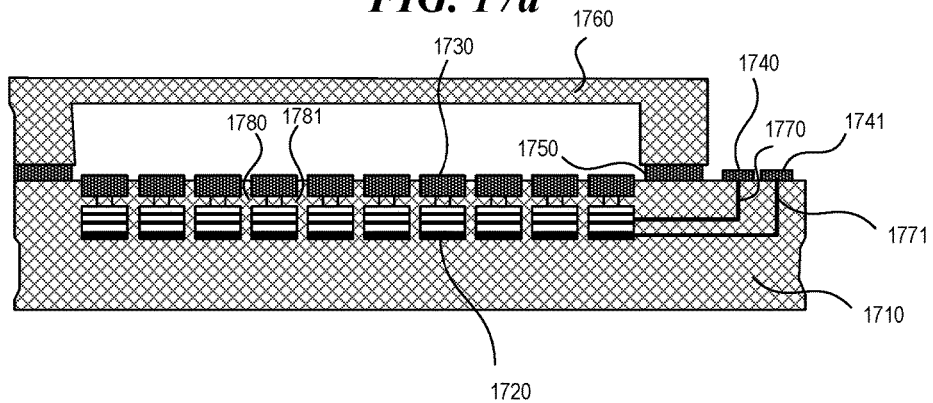
FIG. 17a to FIG. 17b are schematic diagrams of wafer level packaging process permitting wafer level testing with monolithic fabrication of CMOS and NEMS and bonding of CMOS and NEMS wafers, respectively.

In the monolithic fabrication, CMOS can be fabricated first and then NEMS are fabricated on top of CMOS or they are fabricated in the reverse order. In the CMOS first case, the temperature limitations must be respected during processing of NEMS structures in order to avoid damaging CMOS circuitry. Normal CMOS processing does not allow processing temperatures above about 425 deg C. The resulting packaged sensors have the structure shown schematically in FIG. 17a. CMOS circuits 1720 are fabricated on the silicon substrates 1710, including metal lines 1770 and 1771 which connect the CMOS circuits to the external electronics using pads 1740 and 1741. When the metal lines 1770 and 1771 are fabricated, the metal lines and electrical via interconnects 1780 and 1781 are built to connect CMOS 1720 to NEMS 1730. The cover wafer 1760 with the cavities that will reside above NEMS sensors are formed. The pre-cuts are included in the cover wafer in the regions that will end up above the electrical input-output pads 1740 and 1741, so that dicing through the cover wafer can be completed before the dicing blade gets into vicinity of the electrical pads. The cover wafer 1760 can also contain patterns of organic or inorganic material 1750 that is used to bond CMOS-NEMS wafer to the cover wafer. The seal normally contains input and output openings for exposure of sensing surfaces to gas or liquid containing ligands or for their flow through the detection cavity or for the optional removal of gas or liquid. The bonding of two wafers is performed preferably at wafer level, even though bonding of cover chips to CMOS-NEMS wafer is also acceptable. When the cover wafer is transparent to near ultraviolet (UV) light, then UV curing can be used to minimize outgassing that occurs during thermal curing of organic sealing materials. The dicing is performed only partially through the cover wafer 1760 and the sensor wafer 1710 while cover and sensor wafers are sealed on the periphery. Alternatively, dicing that is performed without the presence of liquids, such as laser dicing can be used. This way, the sensors are not exposed to dicing fluids that would damage the sensors. The cover wafer strips above electrical pads are removed while the sensor wafer is still in one piece. Next, the wafer level testing of CMOS and NEMS is performed which identifies good and bad sensors and reduces the cost of subsequent processing of these sensors into the sensing system. The final step involves the separation of the bonded units into individual sensor dies.

In the case of NEMS first and CMOS second fabrication, there would not be limit on processing temperatures of NEMS or their exposure to chemicals that can affect CMOS. This option, however, has a number of other limitations. NEMS devices have to have their surfaces exposed for sensing, so that interaction of ligands with receptors can take place on sensor surfaces. When CMOS would be built adjacent to NEMS, NEMS would have to be interconnected to CMOS with complicated network of metal lines and vias.

The alternative fabrication relies on completion of NEMS structure on one wafer and CMOS circuitry on another wafer and then bonding complementary devices on these two wafers together electrically and mechanically. The electrical bonding can be performed using wafer level bonding of flipped CMOS wafer with NEMS wafer, wafer level bonding with silicon through vias, flip chip bonding of CMOS (or NEMS) chips to the NEMS (or CMOS) wafers respectively or flip chip bonding CMOS and NEMS chips or wire bonding between stacked CMOS and NEMS chips. The preferred method relies on wafer level bonding of CMOS and NEMS wafers because the electrical resistances and parasitic capacitances can be minimized and the cost of bonding can be kept to a minimum.

Figure 17B:
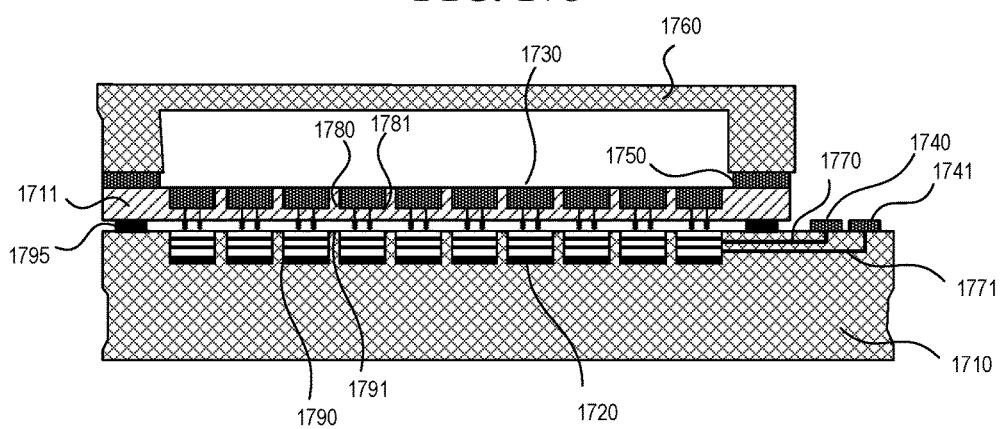

In one embodiment shown in FIG. 17b, the NEMS are fabricated on wafer 1711, the wafer is thinned down and through silicon vias 1780 and 1781 are formed in this wafer. The CMOS wafer 1710 with circuits 1720 is fabricated in the standard way, having the metal lines and input-output electrical pads 1740 and 1741. Subsequently, the electrical interconnects 1790 and 1791 are formed by bonding the CMOS wafer 1710 to NEMS wafer 1711.

In one embodiment, the electrical pads of the CMOS wafer 1740 and 1741 and the electrical CMOS-NEMS interconnects 1790, 1791 in FIG. 17b (or NEMS wafer) are coated with eutectic alloy 1795 such as AuSn, while the second electrical pads on NEMS wafer are covered with Au films in order to prevent the oxidation of their surfaces. The CMOS wafer 1710 and NEMS wafer 1711 are aligned and bonded together by heating the wafers above eutectic temperature to allow solder reflow and formation of the electrical and mechanical contacts.

In another embodiment of wafer bonding, the electrical contacts 1790, 1791 on one wafer, usually CMOS wafer 1710, are formed with the standard material—Al alloy. The second set of electrical contacts above vias 1780, 1781 is formed on NEMS wafer 1711 using Ge in order to enable the formation of AlGe compound after heating the wafers above the critical temperature. This way, CMOS wafer is fabricated with the standard process, without using materials such as Au that are generally incompatible with CMOS fabrication.

During processing that makes the electrical interconnects between NEMS and CMOS wafers, the cavities between NEMS structure and CMOS circuit can be formed at the same time or separately. In the FIG. 17b, the separate cavity wafer 1760 is bonded to the CMOS-NEMS sandwich with sealant 1750 described earlier. Subsequently, the wafers are diced partially while they are sealed on the wafer periphery and cleaved in order to separate them into individual chips. Each chip contains input and output openings so that the gas or liquid can be transported through the structure. The chips are connected to microfluidic structures that contain the valves and pumps to transport the gas or liquid with ligands to be detected through the sensor cavities.

When the electrical interconnects are formed at elevated temperatures, the functionalization of sensor surfaces with receptors is typically performed after bonding, as some receptors can be damaged or altered by exposure to high temperatures.

Another method of electrical bonding of NEMS and CMOS relies on attaching NEMS or CMOS chips on CMOS or NEMS wafers respectively or on stacking of NEMS and CMOS chips and then wire bonding between electrical pads on the individual chips. The epoxy seal between two chips can create the detection cavity above NEMS structure, while allowing for the inlet and outlet for the introduction of species in gaseous or liquid medium. This option permits functionalization of the sensor structures with receptors before bonding because the epoxy bonding can be performed at near ambient or elevated temperatures. The bonding can be done with thermal or UV curing of epoxy. Receptors present on NEMS surfaces do not get altered or damaged in thermal curing at mildly elevated temperatures or during UV curing, as receptors can be shielded with UV blocking film, if necessary. UV bonding is usually associated with very low outgassing of organic material which minimizes interferences with receptors or ligands. The example of the suitable epoxy for the sealing applications with UV bonding and low outgassing is Kyoritsu 9282 and for thermal curing benzo-cyclo-butene from Dow Chemical.

When higher temperatures are used for eutectic bonding with formation of AlGe or AuSn or other eutectic bonds, receptors present on NEMS surfaces can be modified or destroyed, and in these cases, the functionalization has to take place only after the bonding has been completed.

Figure 19A:
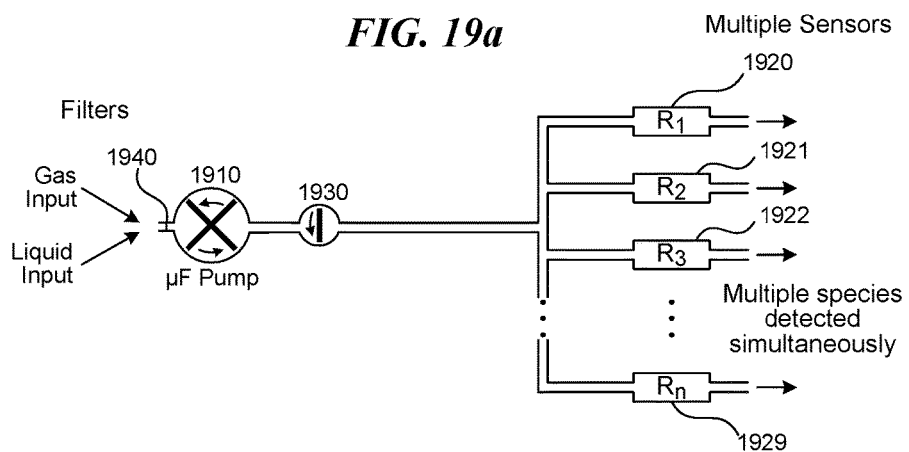
FIG. 19a to FIG. 19b depict schematic architectures of microfluidic front end for the detection of single and multiple species in multiple channels, respectively.
Figure 19B:
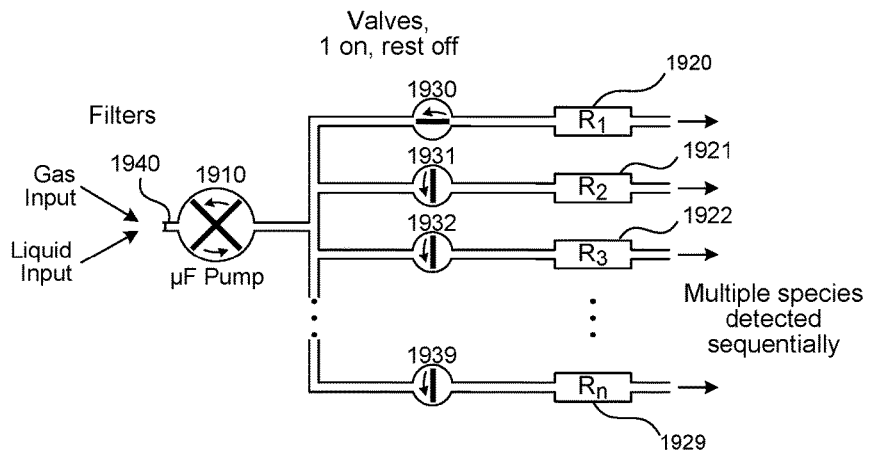
Figure 20:
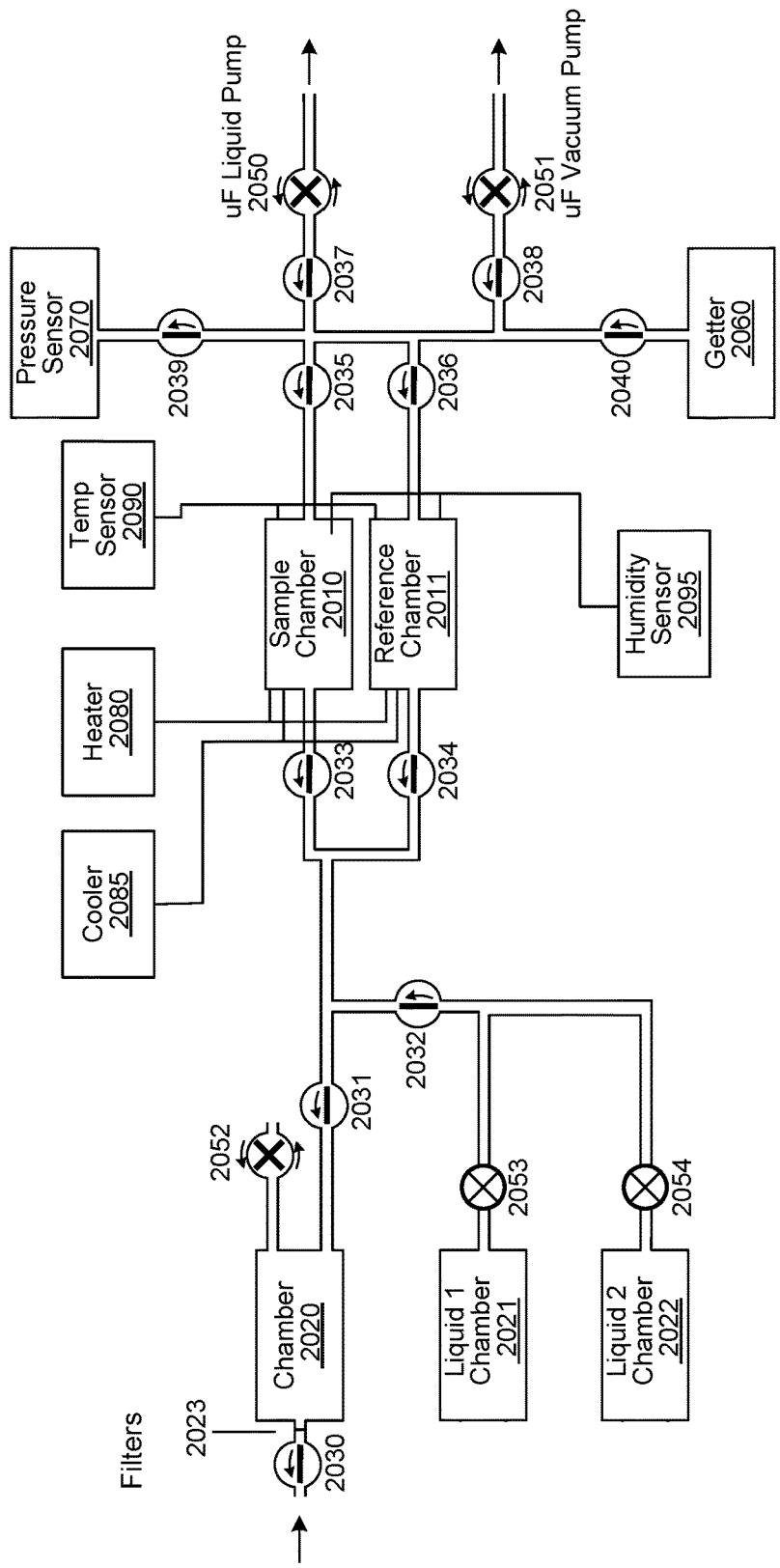
FIG. 20 represents outline of the system architecture with freeze drying or critical point drying and detection at low pressure or vacuum.

The system architecture for the detection of chemical and biological species is shown in FIGS. 18, 19 and 20. The system has the front end that includes sample introduction or preparation 1810, the NEMS sensor 1820, and electrical circuitry 1830 described above and the back end that includes signal processing electronics 1840 and interface or communication links 1850.

In order to achieve very high sensitivity, the resonance of the sensor has to have as high quality factor as possible. The quality factor, Q, is usually defined as the ratio of the resonant frequency, f, divided by the width of the resonance in the frequency domain, $\Delta f_w$, $$Q = f/\Delta f_w.$$

The mass, m, that can be resolved is proportional to $$m = M/Q,$$

the ratio of the effective mass of the sensor M and quality factor Q.

The quality factor Q of the resonator is the highest in the vacuum and it decrease by a factor of 100 to 1000 in air at ambient pressures and by a factor of 1000 or more in the liquids. All species of interest here are present either in the gaseous form or liquid form and the detection with the gas or liquid surrounding the resonators would yield low resolution for detected species.

In order to achieve high sensitivity, the low pressure or vacuum environment has to be created after exposure of the sensors to the ligands present in gas at atmospheric pressure or in liquids. Additionally, it is required to have ligand-receptor interactions that are not reversed when the resonator with ligand-receptor pairs is exposed to suspending liquid removal, pumping or vacuum.

The sample introduction or preparation sub-system is expanded on in FIG. 19. The essential component of this sub-system is the pump 1910, usually of piezoelectric or microfluidic variety. The pump 1910 allows creation of low pressure or vacuum environment before and after sample introduction. The pump 1910 can be physically located at the front end or back end of the sample preparation subsystem. The pump 1910 also permits the sensor to be exposed to the large volume of gas or liquid with suspended species compared to the internal volume of sensing chambers, if necessary. If only gaseous species are being detected, the system would include the filter for water or other suitable filters 1940.

In one case, shown in FIG. 19a, a microfluidic pump 1910 supplies gas or liquid with ligands to multiple channels with sensor arrays functionalized with receptors $R_1, R_2, \ldots R_n$ labeled as 1920, 1921, . . . 1929 for the detection of ligands $L_1, L_2, \ldots L_n$. Each sensor array contains a large number of individual sensors, typically between $10^3$ to $10^7$ individual sensors, in order to improve signal to noise ratio, and therefore the sensitivity of detection. This architecture allows simultaneous detection of multiple species.

In the case of liquid suspended ligands, the micropump 1910 provides introduction of liquid without species, with the valve 1930 in the open position. Once the exposure to liquid is completed, the valve 1930 is closed, liquid removed and pressure lowered as outlined below, and the reference measurement taken. Next, the microvalve 1930 is open again to allow the flow of the same fluid with dispersed or suspended ligands over the sensors, using micropump 1910. The washing step with the suspending liquid is added if necessary. Then, liquid is removed and pressure lowered as described below, using the micropump and valves not shown in FIG. 19a.

In the case of species present in the gas phase, the reference signal is established initially, before the exposure to gas containing monitored species, at low pressure or vacuum, while the valve 1930 is closed. During exposure of sensors to gaseous sample, the valve 1930 is open. After exposure, the valve 1930 is closed again, while the pressure is suitably lowered before measurements using micropump and valve at the back end of the system, not shown in FIG. 19a. Depending on the volume of gas required for exposure of the sensor, the front end micropump 1910 can be included or omitted.

Another microfluidics architecture is outlined in the FIG. 19b for the detection of multiple species sequentially. The system contains microfluidics pump 1910 and the multiple sensors 1920, 1921, . . . 1929 for detection of ligands $L_1, L_2, \ldots L_n$. The microvalves 1931, . . . 1939 are all in the closed positions except one valve, such as 1930 for detection of ligands $L_1$. Subsequently, the microvalve 1930 is closed, the microvalve 1931 is open while the rest of microvalves 1932, . . . 1939 are also closed so that the ligand $L_2$ is detected, etc. If the species are suspended in the liquid, another microvalve similar to the diverting microvalve in FIG. 19a is added to the system. As with architecture 19a, the micropump 1910 is part of the system in order to supply larger amount of gas or liquid for the detection, if necessary. The lowering of pressure before measurements and removal of liquids required for the sensitive detection is detailed below.

When the resonator is exposed to the liquids that are to be subsequently removed, the capillary forces created by the contact between liquid and solid are strong enough to displace or distort the resonator so much that the permanent static forces (stiction) can bring movable parts into contact with stationary parts of the resonator and keep the movable part of resonator in the solid contact with the surroundings, making the resonator inoperable. In other cases when extreme stiction does not occur, the resonant structure may be distorted and the resonant frequency altered, making such a sensor unsuitable for detection. The removal of liquids and transition to low pressure or vacuum has to be managed so that these degradation mechanisms are avoided or minimized.

The solutions allowing preservation of high Q factor for the measurements, after exposure of sensors to the liquid, rely on freeze drying or critical point drying.

In freeze drying, the material is brought around the triple point, avoiding the direct liquid-gas transition typical in normal drying. It is important to cool the material below its triple point, the lowest temperature at which the solid, liquid and gas phases of the material coexist. This ensures that sublimation rather than melting will occur in the following steps.

The freezing can be done rapidly so that formation of larger crystals that can damage the biological materials or NEMS structures is avoided. Usually the freezing temperatures below −10 deg C. are used. During the primary drying phase, the pressure is lowered and enough heat is supplied for the ice to sublimate. The amount of heat necessary is determined by the sublimating molecules' latent heat of sublimation.

The secondary drying phase aims to remove remaining adsorbed water molecules, since the ice was removed in the primary drying phase. This part of the freeze-drying process is governed by the material's adsorption isotherms. In this phase, the temperature is raised higher than in the primary drying phase, and can even be above 0 deg C. for water based materials, to break any physico-chemical interactions that have formed between the water molecules and the frozen material. Usually the pressure is low during this stage to encourage desorption.

The system for freeze drying is shown in FIG. 20. Liquid chambers 2021 and 2022 and valves 2032, 2053 and 2054 are not required for freeze drying; they are used primarily for critical point drying described below. The key components of the freeze drying system are sample chamber 2010 and reference chamber 2011 with the arrays of resonators functionalized to react with the target, cooling system 2085, heater 2080 and the air pump 2051. The system including all valves, pumps, cooler and heater is managed by the microprocessor using data from the temperature sensor 2090, the pressure sensor 2070 and humidity sensor 2095. The pump 2051 can be build using piezoelectric actuators or microfluidic technology. The cooler 2085 is based on Peltier effect that removes heat by passing current through the junction between two dissimilar materials.

The detection starts with taking reference data with the sample chamber 2010 and reference chamber 2011 at low pressure or vacuum. Next, the liquid sample is introduced into sample chamber 2010 and suspending liquid without target species into the reference chamber 2011. After the reaction between the target molecules and the receptors attached to the resonators occurred in the sample chamber 2010, temperature is lowered using the cooler 2085 and pressure is decreased using the micropump 2051 to start sublimation of the liquid. Once the liquid has been removed, temperature is raised moderately to allow desorption of adsorbed water, while the pumping on the system. When the pressure is the same as before the sample introduction, in the sample and reference chambers 2010 and 2011, the measurements of resonant frequencies of all resonators are repeated and the differences between before and after frequencies are determined.

Alternative way to remove the liquid from the sample and reference chambers 2010 and 2011 without stiction and without change of resonant structures is critical point drying. The initial liquid is first substituted in multiple steps or in continuously varying steps with the mixture of the initial liquid and the second liquid until the initial liquid is removed. The second liquid is mixed with the third fluid chosen so that it has the coexistence of liquid and gas simultaneously at critical temperature which allows the liquid removal without condensation of this liquid and without appearance of capillary forces responsible for stiction. The third liquid is allowed to fully replace the second liquid. When the third liquid is completely removed, the gas of the third suspending liquid is pumped out so that the low pressure or vacuum environment is created for sensing. The temperature of the system can be raised moderately, so that the removal of gas adsorbed on the sensor is accelerated. Another condition has to be satisfied with these sensors. Preferably no or minimal number of reacted ligand-receptor pairs or reacted ligands should be removed from the sensor with the exposure to the second and third liquid. The temperature can be only high enough not to lead to the thermal desorption of reacted ligand-receptor pairs or to their degradation.

The microfluidic system that performs the critical point drying transition from liquid to vacuum is shown schematically in FIG. 20.

The microfluidic system has the following structure and operation. The sensing sample chamber 2010 and reference chamber 2011 contain the array of electrostatic or piezoelectric resonant sensors and are connected to the sample injection chamber 2020, the liquid 1 chamber 2021 and liquid 2 chamber 2022 with the series of on-off valves 2031 and 2032 and metering valves 2053 and 2054. Liquid 1 in chamber 2021 is the replacement liquid and liquid 2 in chamber 2022 is the critical point drying liquid. Additional liquid chamber with the suspending liquid for the ligands but without any such ligands can be also included if washing with the suspending liquid is desired. The sample chamber 2010 and reference chamber 2011 are also connected to the microfluidic liquid pump 2050 and the microfluidic vacuum pump 2051 with the set of on-off valves 2035-2038. In addition, the getter chamber 2060 and the pressure sensor 2070 are attached to the sample chamber 2010 and reference chambers 2011 with the set of microfluidic valves. The suitable filters 2023 can be also included at the front end of the system. The humidity sensor 2095 and filters 2023 can also be added to the system.

Fluids suitable for critical point drying include carbon dioxide (critical point of 31 deg C. and 7.4 MPa) and Freon (25 to 30 deg C. and 3.5 MPa.

In most processes, acetone or ethylene is first used to wash away all water, exploiting their complete miscibility. The acetone is then washed away with high pressure liquid carbon dioxide. The liquid carbon dioxide is then heated until its temperature goes beyond the critical point, at which time the pressure can be gradually released, allowing the gas to escape and leaving a dried resonators. The eventual pressure does not have to be very low, as the quality factor Q does not increase significantly once the pressure is below 10 torr to 1 torr, depending on the frequency of the resonator. The getter might be included in the system in order to facilitate removal of water or gas residues.

When the ligands are being sensed in the presence of suspending liquid, the liquid 1 chamber 2021, the liquid 2 chamber 2022, getter chamber 2060, the pressure sensor 2070, microfluidic vacuum pump 2051 and several metering and shut off valves do not have to be included in the microfluidic system.

The detection process starts with establishing the initial (before exposure) differences between resonant frequencies of all sample sensors and resonant frequencies of reference sensors. When the measurements are to be carried out in the liquid or in the gas, the sampling chamber 2010 and the reference chamber 2011 can be filled with the gas or liquid 1 and the initial frequency differences are taken just before the sample detection starts so that long term drifts and temperature variations can be canceled out to the first order. When the measurements are intended to be performed in vacuum at higher sensitivities with higher quality factors, the sampling and reference chambers are kept under low pressure or vacuum or evacuated just before the detection starts, again to establish the initial frequency differences. The evacuation is performed by opening the valves 2035, 2036 and 2038 and activating the vacuum pump 2051.

The reference chamber 2011 is kept under the same conditions as those that were used in taking the before exposure signals, it means with the gas, liquid or vacuum. When the resonant frequency differences between sample sensors after exposure to ligands and reference sensors are being detected, the reference sensor signal is again being mixed with the sample sensor signals using the superheterodyne detection method. The frequency differences before and after exposure are then subtracted to yield the actual frequency decrease associated with the detection of presence of specific ligand, as described earlier.

When the high sensitivity measurements are required, the following sequence of steps is used:

i. The low pressure or vacuum is established in the sample 2010 and reference 2011 sensor chambers using microfluidics vacuum pump 2051.
ii. The frequency differences between sample and reference sensors are determined by beating the sample electrical vibrational signals against reference signals.
iii. The sample with ligands to be detected is introduced from the sample chamber 2020 into sensing chamber 2010 using microfluidic liquid pump 2050.
iv. The liquid 1 from the chamber 2021 is then flowed through the sample chamber 2010, until suspending liquid is removed. This step is followed by the mixture of liquid 1 and liquid 2, with progressively increasing concentration of liquid 2 until liquid 1 is completely replaced with liquid 2. Subsequently, liquid 2 is removed by critical point drying using liquid pump 2050. The metering valves 2053, 2054 are used to adjust the mixture of liquid 1 and 2.
v. When all liquid 2 has been removed, vacuum pump 2051 is connected to the sample 2010 and reference 2011 chambers to lower the pressure. The getter 2060 can be also connected to the sample 2010 and reference chambers 2011 in order to lower the pressure faster to desired range or to achieve lower pressures. In addition, the chamber temperature can be raised to remove the liquid species that might remain adsorbed on the sensor surfaces.
vi. The step ii. above is repeated to determine frequency difference between sample 2010 and reference sensors 2011 due to interaction of ligands with receptors present on sensors.

Alternatively, before the step i. above, the above cycle can be performed but without ligands by using only suspending liquid.

The above described processes with freeze drying or critical point drying are used in functionalization of resonators with receptors in the fabrication of the sensors.

When the ligands are in the gas phase, significant simplification of the system and measurement process is possible. The chambers 2020, 2021 and 2022, valves 2031, 2032, 2053 and 2054, the pump 2050 and the valve 2037 are not needed. The measurement cycle includes only taking frequency data at the low pressure or vacuum, introduction of the samples, return back to the original pressure using the pump 2051 and then re-measuring the resonant frequencies of all resonators.

In many applications, it is desirable not only to ascertain the presence or absence of ligands of interest but also obtain the kinetics of interactions of ligands with receptors. When the sensing is performed in gas or liquid, then no changes are required to follow interactions as a function of time to quantify association and dissociation time constants from time dependence of mass increases. When high sensitivity is needed and the detection has to be performed in low pressure or vacuum, the cycling between the gas or liquid exposure followed by freeze drying or critical point drying before the measurements are taken as a function of time, would result in very long, complicated detection process. For this reason, the cumulative time dependence is more efficient to get the kinetics data by employing multiple blocks of sensors. The first array of sensors is exposed to ligands in gas or liquid for time period $t_1$, the second array of sensors is exposed for time period of $t_1+t_2$, and nth array of sensors is exposed for time period of $t_1+t_2+ \ldots +t_n$. After each exposure of i-th array of sensors, the freeze drying or critical point drying is applied to the particular block of sensors, if ligands are liquid based, followed by evacuation of i-th array and measurements in low pressure or vacuum. In this process, the kinetics of interactions is determined during time that is equal to the overall exposure time plus one freeze drying or critical point drying cycle time.

The front end that is dedicated to the sample preparation and delivery in the gas or liquid state, may include, apart from microvalves and micropumps, also device for gas or liquid chromatographic separation or electrophoretic separation or the concentrator.

The sensor is normally enclosed in the sealed package or in the package that has the valves closed before the initiation of detection. When it is desired to use the sensor, the seal is broken or the valve is open and the sensor is exposed to external environment, such as for detection of gaseous species—ozone, explosive vapors, breath, etc. or to the detection of species suspended in the liquid.

For direct diagnostics by people without assistance of labs, the system might contain, apart from microfluidic system described above, a microneedle (such as one available from Kumerix) that allows evasive procurement of blood samples with the minimum or no discomfort.

The interface or communication sub-system 1850 can also include the display of data, such as a simple Liquid Crystal Display, memory for storing data such as flash memory and electrical connection to other devices such as cell phone or transmitter with or without receiver for wireless transmission of data.

The above described sensing capabilities can find particular useful application in personalized medicine and personalized wellness monitoring. The personalized medicine would require detailed and frequent analysis of patent's breath, saliva, urine or blood anywhere and anytime, preferably away from the diagnostics lab. In personalized medicine, drugs are optimized and administered according to each individual's unique genetic makeup when needed, as a result of on demand testing. The sensing sub-system can be also used as a monitor of concentration of drugs in the patient, forming a part of the system that controls introduction of medicine to the patient in the closed loop servo system.

Personalized medicine transforms medicine from prescribing treatment based on patent's symptoms to therapies based on patent's genetics and individualized needs. It promises to detect diseases early and treat diseases more effectively and alleviate symptoms.

The above described biomedical NEMS sensors make medical diagnostics and personal wellness monitoring faster, cheaper, portable, wireless and therefore useful for personalized medicine.

What is claimed is:

1. A device, comprising:
   a substrate;
   a sensor comprising of at least two piezoelectric hinges that support an electrode plate having at least one receptor, wherein the piezoelectric hinges reside on electrodes located on the substrate, and the electrode plate and the electrodes are connected to electrical pads on the substrate;
   a driving circuit that supplies an electrical waveform to electrodes and;
   a sensing circuit that detects a change of the resonant response of the sensor as a result of an added mass when at least one receptor interacts with a ligand.

2. The device of claim 1, wherein the change of the resonant response of the sensor includes a change of a frequency and a phase.

3. The device of claim 1, wherein the electrodes and the electrode plate are electrically connected to the driving circuit and the sensing circuit.

4. The device of claim 1, further comprising:
   a driving amplifier configured to amplify driving waveforms supplied by the driving circuit; and
   a sensing amplifier configured to amplify an electrical signal caused by the motion of the electrode plate.

5. The device of claim 1, wherein the change of the resonant response is insensitive to the position on the electrode plate at which at least one receptor interacts with the ligand.

6. The device of claim 1, wherein the change of the resonant response depends on an added mass of the ligand.

7. The device of claim 1, wherein the ligand is a chemical molecule or a biological specie.

8. The device of claim 1, wherein a plurality of the receptors is deposited on the electrode plate by an ink jet process.

9. The device of claim 1, further comprising:
   a microfluidic subsystem configured to reduce gas pressure around the sensor to increase sensitivity of ligand detection.

10. The device of claim 1, further comprising:
    a freeze drying subsystem or a critical point drying subsystem configured to remove liquid from or around the sensor by sublimation.

11. A method for detecting a ligand comprising;
    providing a device which comprises:
      a substrate;
      a sensor comprising of at least two piezoelectric hinges that support an electrode plate having at least one receptor, wherein the piezoelectric hinges reside on electrodes located on the substrate, and the electrode plate and the electrodes are connected to electrical pads on the substrate;
      a driving circuit; and
      a sensing circuit;
    applying a driving waveform to the sensor; and
    detecting a change of a resonant response of the sensor as a result of an added mass when at least one receptor interacts with a ligand.

12. The method of claim 11, wherein the change of the resonant response of the sensor includes a change of a frequency and a phase.

13. The method of claim 11, further comprising:
    determining an identity and a concentration of the ligand based on the change of the resonant response.

14. The method of claim 11, further comprising:
    reducing, by a microfluidic subsystem, a gas pressure around the sensor to increase the sensitivity of ligand detection.

15. The method of claim 11, wherein at least one receptor is attached to the electrode plate at a wafer level.

16. The method of claim 11, further comprising:
    exposing the sensor to two environments which are the same except for the presence of the ligands in the second environment; and detecting a change of the resonant response in a vacuum or a low pressure after exposure to the two environments.

17. The method of claim 11, further comprising:
    detecting the resonant response of at least two sensors in a vacuum or a low pressure;
    exposing the first sensor to an environment containing the ligand;
    exposing the second sensor to the same environment but without the ligand;
    bringing at least two of the sensors to the vacuum or the low pressure;
    detecting the resonant response of the first sensor and the second sensor; and
    subtracting the change in the second sensor resonant response before and after exposure from the change in the first sensor resonant response before and after exposure.

18. A system for detecting ligands, comprising:
    an array of devices on a common substrate, wherein each of the devices further comprises:
      a substrate;
      a sensor comprising of a at least two piezoelectric hinges that support an electrode plate having at least one receptor, wherein the piezoelectric hinges reside on electrodes located on the substrate, and the electrode plate and the electrodes are connected to electrical pads on the substrate;
      a driving circuit; and
      a sensing circuit that detects the change of the resonant response of the sensor as a result of an added mass when at least one receptor interacts with a ligand.

19. The system of claim 18, further comprising:
    a multiplexer to control the driving circuits and the sensing circuits; and
    processing electronics to determine a mass change of the sensors after exposure to a sample containing the ligands.

20. The system of claim 18, further comprising:
    a microfluidic pump configured to reduce a gas pressure around the sensors to increase sensitivity of ligand detection.

21. The system of claim 18, further comprising:
    a freeze drying subsystem or a critical point drying subsystem configured to remove a liquid from around the sensors by sublimation to increase sensitivity of ligand detection.

* * * * *